United States Patent [19]
Tam et al.

[11] Patent Number: 5,994,061
[45] Date of Patent: Nov. 30, 1999

[54] DNA CONSTRUCTS AND METHODS FOR SCREENING FOR INCREASED EXPRESSION OF HUMAN APO AI GENE

[75] Inventors: Shui-Pang Tam; Xia Zhang, both of Kingston, Canada

[73] Assignee: Queen's University at Kingston, Kingston, Canada

[21] Appl. No.: 08/536,559

[22] Filed: Sep. 29, 1995

[51] Int. Cl.$^6$ .................................................... C12Q 1/68
[52] U.S. Cl. ................................ 435/6; 435/8; 435/370; 536/24.1
[58] Field of Search ................................ 435/6, 7, 172.3, 435/240, 91.1, 91.2, 63, 69.9, 8, 370; 536/23.5, 23.1, 24.1

[56] References Cited

U.S. PATENT DOCUMENTS

| | | | |
|---|---|---|---|
| 4,393,133 | 7/1983 | Knowles et al. | 435/6 |
| 4,677,057 | 6/1987 | Curtiss et al. | 436/518 |
| 4,801,531 | 1/1989 | Frossard | 435/6 |
| 4,828,986 | 5/1989 | Smith et al. | 435/7.34 |
| 4,943,527 | 7/1990 | Protter et al. | 435/69.6 |
| 5,059,528 | 10/1991 | Bollen et al. | 435/69.4 |
| 5,220,006 | 6/1993 | Ross et al. | 536/24.1 |
| 5,320,968 | 6/1994 | Seman | 436/71 |
| 5,378,822 | 1/1995 | Bradfield et al. | 536/23.5 |
| 5,408,038 | 4/1995 | Smith et al. | 530/359 |
| 5,580,722 | 12/1996 | Foulkes et al. | 435/6 |

OTHER PUBLICATIONS

Sastry et al. 1988 Mol. Cell. Biol. 8(2): 605–614.
Fujii–Kuriyama et al. 1986 Proc. Nat'l. Acad. Sci USA 83: 8044–8048.
Chen, et al., Circulation 90, I–570, 3069 (Oct. 1994).
Karathanasis et al., Nature (London) 304: 371–373 (1983).
Breslow et al., Proc. Nat. Acad. Sci. USA 79: 6861–6865 (1982).
Sogawa et al., Proc. Natl. Acad. Sci. USA 83: 8044–8048 (1986).
Fujisawa–Sehara et al., Proc. Natl. Acad. Sci. USA 85: 5859–5863 (1988).
Sigurdsson et al., Arteriosclerosis and Thrombosis 12: 1017–1022 (1992).
Tuteja et al., FEBS Letters 304: 98–101 (1992).
Jeenah et al., Mol. Biol. Med. 7: 233–241 (1990).
Pagani et al., J. Lipid Res. 31: 1371–1377 (1990).
Sastry et al., Mol. Cell. Biol. 8: 605–614 (1988).
Widom et al., Mol Cell. Biol. 11: 677–687 (1991).
Smith et al., J. Clin. Invest. 89: 1796–1800 (1992).
Papazafiri et al., J. Biol. Chem. 266: 5790–5797 (1991).
Angotti et al., J. Biol. Chem. 269: 17,371–17,374 (1994).
Tam, Atherosclerosis 91: 51–61 (1991).
Tam et al., J. Biol. Chem. 260: 1670–1675 (1985).
Tam, Alcohol. Clin. Exp. Res. 16: 1021–1028 (1992).
Tam et al., Atherosclerosis 105: 235–243 (1994).
Frick et al., N. Engl. J. Med. 317: 1237–1245 (1987).
Manninen et al., Circulation 85: 37–45 (1992).
Brown, Am. J. Catdiol. 66: 11A–15A (1990).
Gordon et al., Am. J. Med. 62: 707–714 (1977).
Stampfer et al., N. Engl. J. Med. 325: 373–381 (1991).
Kussi et al., Arteriosclerosis 7: 421–425 (1987).
Moll et al., Am. J. Human Genet. 44: 124–139 (1989).
Hamsten et al., Atherosclerosis 60: 199–208 (1986).
Gotto et al., Methods Enzymol. 128: 3–41 (1986).
Miller et al., Nature (London) 314: 109–111 (1985).
Glomset. Adv. Intern. Med. 25:91–116 (1980).
Rubin et al., Nature (London) 353: 265–267 (1991).
Knuiman et al., Arteriosclerosis 7: 612–619 (1987).
Berg et al., Clin. Chim. Acta 161: 165–171 (1986).
Davidson et al., J. Lipid Res. 29: 1511–1522 (1988).
Haddad et al., J. Biol. Chem. 26: 13,268–13,277 (1986).
Staels et al., J. Lipid Res. 30: 1137–1145 (1989).
Luoma et al., Acta Med. Scand. 214: 103–109 (1983).
Luoma, Pharm & Toxic. 65: 243–249 (1988).
GeneLight™ Plasmids Technical Manual, Promega Corporation, WI pp. 1–39 (1991).
Gorman et al., Mol. Cell Biol. 2: 1044–1051 (1982).
Scatchard, Ann. N.Y. Acad. Sci. 51: 660–672 (1949).
Wilson et al., Plasmid 33: 198–207 (1995).
Colbere–Garapin et al., J. Mol. Biol. 150: 1–14 (1981).
Jimenz et al., Nature (London) 287: 869–871 (1980).
de Wet et al., DNA 3, 437–447 (1984).
PCR Protocols: A Guide to Methods and Applications, Innis et al. (ed.), Academic Press, San Diego, CA pp. 13–20 (1990).

(List continued on next page.)

*Primary Examiner*—James Ketter
*Assistant Examiner*—Irem Yucel
*Attorney, Agent, or Firm*—Carol Miernicki Steeg

[57] ABSTRACT

Methods for screening for a drug that increases expression of the human apolioprotein (apo) AI gene and related DNA constructs. A first method has the steps of: (a) introducing into mammalian cells a DNA construct including, functionally joined together in the 5'→3' direction of transcription, (i) at least one copy of a drug-responsive element (DRE) having at least about 80% homology with the DNA sequence 5'-G/C N T/G A/G GCTGGG-3', (ii) a heterologous promoter, (iii) a reporter gene and (iv) an untranslated region including a functional polyadenylation signal; (b) growing a first culture of the cells in the absence of drug; (c) lysing the first culture to produce a first extract; (d) assaying the first extract for activity of a protein encoded by the reporter gene; (e) growing a second culture of the cells in the presence of the drug; (f) lysing the second culture to produce a second extract; (g) assaying the second extract for activity of the protein encoded by the reporter gene; and (h) comparing the activities of the first extract and the second extract. A second method uses a different DNA construct including (i) a promoter region of the human apo AI gene including at least one copy of a drug-responsive element (DRE) having at least about 80% homology with the DNA sequence 5'-G/C N T/G A/G GCTGGG-3', (ii) a reporter gene and (iii) an untranslated region including a functional polyadenylation signal. A third method involves stably maintaining the introduced DNA in the cells.

20 Claims, 10 Drawing Sheets

OTHER PUBLICATIONS

Sambrook et al.,. Molecular Cloning: A Laboratory Manual (2nd edition), Cold Spring Harbor Laboratory, Cold Spring Harbor, NY pp. 14.1–14.21 (1989).
Bartalena, Mol. Endocrinol. 6: 935–942 (1992).
McKnight et al., J. Biol. Chem. 254: 9050–9058 (1979).
Dignam et al., Nucl. Acids Res. 11: 1475–1489 (1983).
Lowry et al., J. Biol. Chem. 193: 265–275 (1951).
Faisst et al., Nucl. Acids Res. 20: 3–26 (1992).
Whitlock, Jr., Annu. Rev. Pharmacol. Toxicol. 30: 251–277 (1990).
Singh et al., Biotechniques 7:252–261 (1989).

Sequences of Cold Oligonucleotides        Fold of Competition apo AI-DRE:
5'GGCCGGGGCTGGCTTATCAGCCTCCCAGCCCAGACC3'    100

AP 1 (hAORE):
5'GCAGTCACAGTGACTCAGCAGAATCT3'              100

AP 2:
5'GATCGAACTGACCGCCCCGCGGCCCCGT3'            100

DNA CONSTRUCTS AND METHODS FOR SCREENING FOR INCREASED EXPRESSION OF HUMAN APO AI GENE

FIELD OF THE INVENTION

This invention relates to the field of drugs that regulate gene expression. More specifically, the invention relates to drugs that regulate expression of a gene for apolipoprotein AI, and still more specifically, to DNA constructs and methods of screening for such a drug.

BACKGROUND OF THE INVENTION

The major cause of death in many industrialized countries is atherosclerosis, a degenerative disease in which the walls of the arteries slowly become thickened by deposits of fatty material such as cholesterol. The deposits, or plaques, inhibit blood flow, often leading to heart attack or stroke. The personal and economic costs of atherosclerosis, and particularly of the form known as coronary artery disease (CAD), are vast. The economic cost of atherosclerosis has been estimated at 60 billion dollars annually.

Cholesterol is a building block for such hormones as estrogen and testosterone, as well as a fundamental structural component of animal cell membranes. When animal cells are growing and dividing, cholesterol required for new membrane material is transported to the site of growth via the blood. Cholesterol is transported in the blood in lipid-protein particles. The four major classes of such particles are the chylomicrons, the very low density lipoproteins (VLDL), the low density lipoproteins (LDL) and the high density lipoproteins (HDL).

Numerous studies have demonstrated that high concentrations of LDL in the blood plasma strongly correlate with increased risk of CAD. Thus, LDL is popularly called "the bad cholesterol". On the other hand, epidemiological and genetic studies have indicated both that high plasma concentrations of HDL correlate with protection against CAD, and that low plasma concentrations of HDL are involved in the development of atherosclerosis [Gordon et al., *Am. J. Med.* 62: 707–714 (1977); Stampfer et al., *N. Engl. J. Med.* 325: 373–381 (1991); Kuusi et al., *Arteriosclerosis* 7: 421–425 (1987); Moll et al., *Am. J. Human. Genet.* 44: 124–139 (1989); Hamsten et al., *Atherosclerosis* 60: 199–208 (1986)]. Thus, the popular nickname for HDL is "the good cholesterol".

The major protein component of HDL is apolipoprotein (apo) AI, which is believed to promote the process of "reverse cholesterol transport" [Gotto et al., *Methods Enzymol.* 128: 3–41 (1986); Miller et al., *Nature (London)* 314: 109–111 (1985); Glomset, *Adv. Intern. Med.* 25: 91–116 (1980)]. In this process, excess cholesterol is liberated from the peripheral tissues and carried, via HDL, to the liver for degradation. In addition, apo AI acts as a cofactor for the enzyme lecithin-cholesterol acyltransferase (LCAT), which is also involved in reverse cholesterol transport [Gotto et al., *Methods Enzymol.* 128: 3–41 (1986); Miller et al., *Nature (London)* 314: 109–111 (1985); Glomset, *Adv. Intern. Med.* 25: 91–116 (1980)]. Further evidence that apo AI is a strong negative factor for atherosclerosis comes from experiments in which transgenic mice carrying the human apo AI gene were fed a high fat diet. Here, expression of the apo AI transgene and the resulting high levels of human apo AI in the animals' blood appeared to protect against development of fatty streak lesions [Rubin et al., *Nature (London)* 353: 265–267 (1991)]. By extension, if the expression of the apo AI gene in humans could be increased, it would likely protect against deposition of atherosclerotic plaques.

The foregoing and other studies indicate that the regulation of apo AI gene expression is extremely important in controlling the development of CAD. In mammals, apo AI expression is tissue-specific, with synthesis taking place primarily in the liver and intestine [Gotto et al., *Methods Enzymol.* 128: 3–41 (1986)]. Presumably, tissue-specific factors are responsible for this limited expression pattern.

A number of factors have been reported to modulate plasma levels of apo AI and/or HDL cholesterol. These include diet [Knuiman et al., *Arteriosclerosis* 7: 612–619 (1987)], exercise [Berg et al., *Clin. Chim. Acta* 161: 165–171 (1986)], sex hormones [Tam et al., *J. Biol. Chem.* 260: 1670–1675 (1985)], thyroid hormone [Davidson et al., *J. Lipid Res.* 29: 1511–1522 (1988)], ethanol [Tam, *Alcohol. Clin. Exp. Res.* 16: 1021–1028 (1992)] and temporal factors during development [Haddad et al., *J. Biol. Chem.* 26: 13268–13277 (1986); Staels et al., *J. Lipid Res.* 30: 1137–1145 (1989)]. In addition, clinical studies have shown that there is direct relationship between the levels of cytochrome P450 enzymes in the liver and the levels of HDL and apo AI in the blood [Luoma et al., *Acta Med. Scand.* 214: 103–109 (1983); Luoma, *Pharm. & Toxic.* 65: 243–249 (1988)]. Cytochrome P450 enzymes function in the detoxification of aromatic compounds and in bile acid and vitamin D metabolism. The nature of the relationship between hepatic cytochrome P450 levels and plasma apo AI levels is not fully understood.

Clinically, a number of drugs have been used to reduce the risk and/or progression of CAD by altering lipoprotein metabolism. Gemfibrozil (Lopid™), manufactured by Parke Davis of Morris Plains, N.J., is one of the most extensively studied pharmaceutical agents for the treatment of hyperlipidemia [Manninen et al., *Circulation* 85: 37–45 (1992): Brown, *Am. J. Cardiol.* 66: 11 A–15A (1990)]. In patients treated with gemfibrozil, both total and LDL cholesterol levels in the plasma are reduced, whereas HDL cholesterol levels are markedly raised. In the classic Helsinki Heart Study [Frick et al., *N. Engl. J. Med.* 317: 1237–1245 (1987)], the administration of gemfibrozil over a five year period to middle-aged men who were at high risk because of abnormal concentrations of blood lipids resulted in a 34% reduction in coronary disease, relative to a similar group of men who received only a placebo. At least part of this effect may be ascribed to the action of gemfibrozil in significantly raising HDL concentrations.

One of the present inventors has previously reported that the exposure of two human hepatoma cell lines, HepG2 and Hep3B, to gemfibrozil results in a two-fold increase in the level of apo AI mRNA [Tam, *Atherosclerosis* 91: 51–61 (1991)]. Prior to the invention described below, the mechanism of gemfibrozil action in regard to apo AI levels was unknown.

The human apo AI gene is located on the long arm of chromosome 11. The DNA sequence of this gene is identified in Karathanasis et al., *Nature (London)* 304: 371–373 (1983); Breslow et al., *Proc. Nat. Acad. Sci. USA* 79: 6861–6865 (1982); and GenBank accession no. M20656. Cis- and trans-acting elements involved in the regulation of transcription of the apo AI gene have been studied by several groups [Sastry et al., *Mol. Cell. Biol.* 8: 605–614 (1988); Widom et al., *Mol. Cell. Biol.* 11: 677–687 (1991); Papazafiri et al., *J. Biol. Chem.* 266: 5790–5797 (1991); Pagani et al, *J. Lipid Res.* 31: 1371–1377 (1990); Smith et al., *J. Clin. Invest.* 89: 1796–1800 (1992); Sigurdsson et al., *Arteriosclerosis and Thrombosis* 12: 1017–1022 (1992); Tuteja et al., *FEBS Letters* 304: 98–101 (1992); Jeenah et al., *Mol. Biol. Med.* 7: 233–241(1990)]. FIG. 1 shows in block form the organization of the 5' flanking region of the human apo AI gene, according to the results obtained by such groups.

In a first study conducted by Karathanasis and co-workers [Sastry et al., *Mol. Cell. Biol.* 8: 605–614 (1988)], transient transfection assays were used to identify a liver-specific enhancer element located between nucleotides −256 to −41 upstream of the transcription start site (+1) of the human apo AI gene. Evidence was presented that this DNA region contains regulatory elements that are necessary and sufficient for maximal expression of the gene in the human hepatoma cell line HepG2.

In a further study [Widom et al., *Mol. Cell. Biol.* 11: 677–687 (1991)], the same group used gel mobility shift and DNase I footprinting assays to identify three distinct sites within the enhancer, sites A (−214 to −192), B (−169 to −146), and C (−134 to −119), to which transcriptional factors present in HepG2 cells specifically bind. These regions are indicated in FIG. 1 by A*, B* and C*. The researchers found that binding of a factor to a single site in the absence of binding to the others was not sufficient for gene expression. Binding of factors to any two of the sites resulted in low levels of expression. Binding to all three sites was necessary for maximal gene expression. It was hypothesized that protein-protein interactions between the bound transcription factors provided this synergistic effect.

In another fine structure study [Papazafiri et al., *J. Biol. Chem.* 266: 5790–5797 (1991)], Zannis and co-workers identified four DNA regions proximal to the human apo AI gene that were protected against digestion by DNAse I by the binding of factors contained in rat liver nuclear extracts. The protected regions were designated A (−22 to +17), B (−128 to −77), C (−175 to −148) and D (−220 to −190), as shown in FIG. 1. The rat nuclear proteins that bound to the region −220 to −148 (i.e., regions D and C) were identified using in vitro mutagenesis, DNA binding assays and protein fractionation. Both positive and negative regulators were identified.

At least three different groups have studied the effect on apo AI levels of a G to A transition variously identified as occurring at −78 [Pagani et al., *J. Lipid Res.* 31: 1371–1377 (1990); Tuteja et al., *FEBS Letters* 304: 98–101 (1992)], at −76 [Smith et al., *J. Clin. Invest.* 89: 1796–1800 (1992)] and at −75 [Jeenah et al., *Mol. Biol. Med.* 7: 233–241(1990); Sigurdsson et al., *Arteriosclerosis and Thrombosis* 12: 1017–1022 (1992)] relative to the start of transcription of the human apo AI gene. Despite the discrepancy in numbering, the studies seem to concern the same point mutation, in which an Msp I restriction site (CCGG) is destroyed by the substitution of A at the position of the first G. This substitution, which is at the border of region B identified by the Zannis group, occurs naturally in the human population.

The first of these groups, Baralle and co-workers, reported that the presence of the A allele was associated with high HDL cholesterol and apo AI levels in women, but not in men [Pagani et al., *J. Lipid Res.* 31: 1371–1377 (1990)]. They noted that the polymorphism occurred in a 51 bp GC-rich region containing an inverted repeat composed of two 14/15 bp elements. The homology and self-complementarity of the inverted repeats was disrupted when a G, instead of an A, was present at the −78 position. In transient transfection assays using a DNA fragment from −330 to +1, the A allele demonstrated about two-fold higher activity than the G allele [Tuteja et al., *FEBS Letters* 304: 98–101 (1992)]. However, when a larger DNA fragment from −1469 to +397 was used, the two alleles displayed similar transcriptional levels.

A second group, Breslow and co-workers, reported that patients that were G/A heterozygotes at this position displayed significantly lower apo AI production rates than G/G homozygotes [Smith et al., *J. Clin. Invest.* 89: 1796–1800 (1992)]. (In a human subject, the apo AI production rate takes into account not only the level of apo AI synthesis, but also its levels of intracellular transport, secretion and plasma clearance.) Despite their different production rates, no difference was found in HDL cholesterol or apo AI levels between the two groups of patients. When the expression levels of the two alleles were compared in transient transfection assays employing a 325 bp fragment of the apo AI gene, the expression level of the A allele was found to be only approximately 68% of the expression level of the G allele. These results are in direct contrast with those of the Baralle group. However, like the Baralle group, the Breslow group also explained their results in terms of the effect of the point mutation on the inverted repeats. They speculated that the increased complementarity of the inverted repeats by the presence of an A at −76 might allow for the formation of a DNA secondary structure that might interfere with protein-protein interactions of the transcriptional apparatus.

A third group, Humphries and co-workers, reported that men having high plasma apo AI levels carried the A allele more than twice as often as men with lower plasma apo AI levels [Jeenah et al., *Mol. Biol. Med.* 7: 233–241(1990)]. In addition, men carrying the A allele displayed significantly higher HDL cholesterol levels. Thus, this work contrasts with both the Baralle group's findings, in which only women were affected, and the Breslows group's findings, in which no difference in apo AI and HDL cholesterol levels were identified between carriers of the two alleles. In a subsequent study, the Humphries group went on to report that the protection against risk of CAD that had been observed for men carrying the A allele was abolished if the men smoked [Sigurdsson et al., *Arteriosclerosis and Thrombosis* 12: 1017–1022 (1992)]. That is, male smokers carrying the A allele were found to have approximately the same apo AI and HDL cholesterol levels as men carrying the G allele.

Thus, although a great deal of work has been done to date on the regulation of expression of the human apo AI gene, much clarification is still required. The various cis- and trans-acting factors involved and the nature of their interactions need to be identified and elucidated. In particular, the mechanisms by which various drugs, for example, gemfibrozil, influence apo AI expression are heretofore unknown. Given the protection that high plasma apo AI levels provide against CAD, it would be extremely desirable to understand how a particular drug could increase apo AI expression. A convenient method and tools for screening for such a drug would also be extremely desirable.

SUMMARY OF THE INVENTION

The present invention provides, in a first aspect, a purified DNA construct including, functionally joined together in the 5'→3' direction of transcription:

at least one copy of a drug-responsive element (DRE) having at least about 80% homology with the DNA sequence 5'-G/C N T/G A/G GCTGGG-3'(SEQ ID NO:5), a heterologous promoter, a reporter gene, and an untranslated region including a functional polyadenylation signal.

In a second aspect, the invention provides mammalian cells into which a DNA construct according to the invention has been introduced. The cells may be of hepatic or intestinal origin. The construct may be stably maintained by the cells.

In a third aspect, the invention provides the use of mammalian cells into which a DNA construct according to the invention has been introduced, to screen for a drug that increases expression of an apo AI gene.

In a fourth aspect, the present invention provides a method of screening for a drug that increases expression of a gene for apolipoprotein AI (apo AI), including the following steps:
  introducing into mammalian cells a DNA construct including, functionally joined together in the 5'→3' direction of transcription, (I) a promoter region of the human apo AI gene including at least one copy of a drug-responsive element (DRE) having at least about 80% homology with the DNA sequence 5'-G/C N T/G A/G GCTGGG-3', (ii) a reporter gene and (iii) an untranslated region including a functional polyadenylation signal;
  growing a first culture of the cells in the absence of drug;
  lysing the first culture to produce a first extract;
  assaying the first extract for activity of a protein encoded by the reporter gene;
  growing a second culture of the cells in the presence of the drug;
  lysing the second culture to produce a second extract;
  assaying the second extract for activity of the protein encoded by the reporter gene; and
  comparing the activities of the first extract and the second extract.

In a fifth aspect, the present invention provides a method of screening for a drug that increases expression of a gene for apolipoprotein AI (apo AI), including the following steps:
  introducing into mammalian cells a DNA construct including, functionally joined together in the 5'→3' direction of transcription, (I) at least one copy of a drug-responsive element (DRE) having at least about 80% homology with the DNA sequence 5'-G/C N T/G A/G GCTGGG-3', (ii) a heterologous promoter, (iii) a reporter gene and (iv) an untranslated region including a functional polyadenylation signal;
  growing a first culture of the cells in the absence of drug,
  lysing the first culture to produce a first extract;
  assaying the first extract for activity of a protein encoded by the reporter gene;
  growing a second culture of the cells in the presence of the drug;
  lysing the second culture to produce a second extract;
  assaying the second extract for activity of the protein encoded by the reporter gene; and
  comparing the activities of the first extract and the second extract.

In a sixth aspect, the present invention provides a method of screening for a drug that increases expression of a gene for apolipoprotein AI (apo AI), including the following steps:
  introducing into mammalian cells a DNA construct including, functionally joined together in the 5'→3' direction of transcription, (I) at least one copy of a drug-responsive element (DRE) having at least about 80% homology with the DNA sequence 5'-G/C N T/G A/G GCTGGG-3', (ii) a heterologous promoter, (iii) a reporter gene and (iv) an untranslated region including a functional polyadenylation signal;
  maintaining the introduced DNA construct stably in the cells;
  lysing a first culture of the cells containing the stably maintained DNA construct, which has been grown in the absence of drug, to produce a first extract;
  assaying the first extract for activity of a protein encoded by the reporter gene;
  lysing a second culture of the cells containing the stably maintained DNA construct, which has been grown in the presence of the drug, to produce a second extract;
  assaying the second extract for activity of the protein encoded by the reporter gene; and
  comparing the activities of the first extract and the second extract.

In a seventh aspect, the invention provides a transcription factor that binds to the DNA sequence 5'-G/C N T/G A/G GCTGGG-3'.

It is an object of the present invention to characterize the mechanisms through which expression of the human apo AI gene is regulated. It is a further object to identify agents—drugs and transcription factors—that influence or mediate expression of the apo AI gene. The invention provides a convenient, efficient and rapid system for screening and identifying drugs that increase apo AI gene expression. The invention additionally contemplates a method of treating a human being or an animal with such a drug. A kit for a system according to the invention could be assembled. The system of the invention could also be automated. According to the invention, the DRE could be used as a reagent for the purification of a transcription factor with which it interacts.

BRIEF DESCRIPTION OF THE DRAWINGS

For a better understanding of the present invention and to show more clearly how it may be carried into effect, reference will now be made by way of example to the accompanying drawings, which illustrate aspects and features according to preferred embodiments of the present invention and in which.

DETAILED DESCRIPTION OF THE PREFERRED EMBODIMENTS

In the course of examining the DNA region upstream of (5'to) the human apo AI gene, the present inventors detected a sequence match with a portion of the DNA region upstream of a cytochrome P450 gene known as CYP1A1. The match involves a GC-rich decanucleotide motif, 5'-G/C N T/G A/G GCTGGG-3'(SEQ ID NO: 5), corresponding to a putative drug response element (DRE). The identification of this element upstream of the CYP1A1 gene was first made by Fujii-Kuriyama and co-workers [Sogawa et al., Proc. Natl. Acad. Sci. USA 83: 8044–8048 (1986)]. It was suggested initially that the DRE located upstream of the CYP1A1 gene may be recognized by the aryl hydrocarbon (Ah) receptor. This has now been shown not to be the case. Prior to the present invention, factors that bind to the DRE or are induced by the DRE have not been identified.

Figure 1:
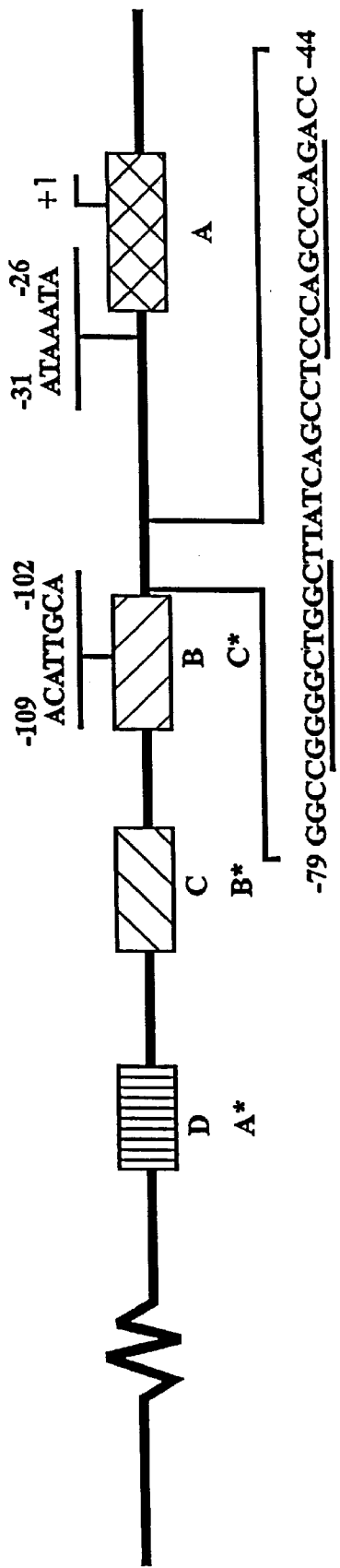
FIG. 1 is a diagrammatic illustration of the 5' flanking region of the human apo AI gene.

FIG. 1 shows the sequence of the 5' flanking region of the human apo AI gene between nucleotides −79 and −44(SEQ ID NO: 8), relative to the transcription start site of the gene. The inventors have detected that two copies of the DRE, spaced 10 nucleotides apart in an imperfect inverted repeat, are present between nucleotides −76 and −46. The upstream element, having the DNA sequence 5'-CGGGGCTGGC-3' (SEQ ID NO: 6), is a 90% match with the DRE consensus sequence 5'-G/C N T/G A/G GCTGGG-3'. The downstream element, having the sense-strand sequence 5'-CCCAGCCCAG-3'(SEQ ID NO: 16), and therefore the sequence 5'-CTGGGCTGGG-3'(SEQ ID NO: 7) on the complementary strand, is a 100% match with the consensus sequence.

It should be understood that two different alleles of this region occur naturally in the human population. FIG. 1 shows the sequence of a first allele, as in Karathanasis et al., Nature (London) 304: 371–373 (1983); Breslow et al., Proc. Nat. Acad. Sci. USA 79: 6861–6865 (1982); and GenBank accession no. M20656. A second allele includes an additional G (guanine), such that the upstream DRE has the sequence 5'-CGGGGCTGG<u>G</u>C-3', effectively increasing the size of the spacer region to 11 nucleotides. (This helps to explain the difference in nucleotide numbering between the Breslow and Humphries groups discussed earlier.) The numbering scheme used in the description below and in the figures is consistent with the first allele.

Previously, one of the present inventors has demonstrated that the exposure of human hepatoma cell lines Hep3B and HepG2 to gemfibrozil results in a two-fold induction of the level of apo AI mRNA [Tam, Atherosclerosis 91: 51–61 (1991)]. The inventors have now demonstrated that the mechanism of this induction involves sequence-specific recognition of the DRE identified between nucleotides −76 to −46 upstream of the apo AI gene by certain transcription factors. Moreover, the inventors have conceived of and created DNA constructs including the DRE that can be used to screen for induction of apo AI expression by gemfibrozil, or by a different, candidate drug. The invention also provides a method of screening for a drug that increases expression of the human apo AI gene. The degree of any induction produced by such a candidate drug can be quantitated according to the method and using a construct or constructs of the invention.

In general terms, a DNA construct of the invention includes, functionally joined together in the 5'→3' direction of transcription: (I) at least one copy of a drug-responsive element (DRE) having at least about 80% homology with the DNA sequence 5'-G/C N T/G A/G GCTGGG-3'(SEQ ID NO: 5), (ii) a heterologous promoter, (iii) a reporter gene, and (iv) an untranslated region including a functional polyadenylation signal.

In some embodiments of the invention, the DNA construct may include at least two drug-responsive elements (DRE) upstream of the reporter gene. The two DRE may be arranged in an inverted repeat relative to each other. The inverted repeat may be perfect or imperfect. A spacer region interposed between the two copies of the DRE may be about 10 nucleotides long.

In some embodiments of the invention, the DRE of the DNA construct may have at least about 90% homology with the DNA sequence 5'-G/C N T/G A/G GCTGGG-3'. In other embodiments, the degree of homology may be 100%. Examples of such sequences are described below and in the figures.

In general terms, the present invention provides a first method of screening for a drug that increases expression of a gene for apolipoprotein AI (apo AI), including the following steps:

(a) introducing into mammalian cells a DNA construct including, functionally joined together in the 5'→3' direction of transcription, (I) a promoter region of the human apo AI gene including at least one copy of a drug-responsive element (DRE) having at least about 80% homology with the DNA sequence 5'-G/C N T/G A/G GCTGGG-3', (ii) a reporter gene and (iii) an untranslated region including a functional polyadenylation signal;

(b) growing a first culture of the cells in the absence of drug;

(c) lysing the first culture to produce a first extract;

(d) assaying the first extract for activity of a protein encoded by the reporter gene;

(e) growing a second culture of the cells in the presence of the drug;

(f) lysing the second culture to produce a second extract;

(g) assaying the second extract for activity of the protein encoded by the reporter gene; and (h) comparing the activities of the first extract and the second extract.

According to the invention, the ability to measure quantitatively the amount of reporter gene product present in an assay permits inference of the amount of expression of the reporter gene that has taken place. The level of expression of the reporter gene will be increased in the situation where a candidate drug interacts with the DRE linked to the reporter gene. If the candidate drug increases reporter gene expression in the assay, it would be expected to increase expression of the naturally occurring human apo AI gene, which carries two copies of the DRE in its 5' flanking region. Higher levels of expression of the reporter gene could thus be taken as a first indication of the potential effectiveness of the candidate drug.

In general terms, the invention also provides a second method of screening for a drug that increases expression of a gene for apolipoprotein AI (apo AI), including the following steps:

(a) introducing into mammalian cells a DNA construct including, functionally joined together in the 5'→3' direction of transcription, (I) at least one copy of a drug-responsive element (DRE) having at least about 80% homology with the DNA sequence 5'-G/C N T/G A/G GCTGGG-3', (ii) a heterologous promoter, (iii) a reporter gene and (iv) an untranslated region including a functional polyadenylation signal;

(b) growing a first culture of the cells in the absence of drug;

(c) lysing the first culture to produce a first extract;

(d) assaying the first extract for activity of a protein encoded by the reporter gene;

(e) growing a second culture of the cells in the presence of the drug;

(f) lysing the second culture to produce a second extract;

(g) assaying the second extract for activity of the protein encoded by the reporter gene; and (h) comparing the activities of the first extract and the second extract.

For both of these methods, it is preferred that the DNA construct is introduced into the cells and the second culture of cells is subsequently grown in the presence of the drug being screened. However, the inventors have found that it is also possible according to the invention to grow the second culture in the presence of the drug prior to introduction of the DNA construct.

In general terms, the invention also provides a third method of screening for a drug that increases expression of a gene for apolipoprotein AI (apo AI), including the following steps:

(a) introducing into mammalian cells a DNA construct including, functionally joined together in the 5'→3' direction of transcription, (I) at least one copy of a drug-responsive element (DRE) having at least about 80% homology with the DNA sequence 5'-G/C N T/G A/G GCTGGG-3', (ii) a heterologous promoter, (iii) a reporter gene and (iv) an untranslated region including a functional polyadenylation signal;

(b) maintaining the introduced DNA construct stably in the cells;

(c) lysing a first culture of the cells containing the stably maintained DNA construct, which has been grown in the absence of drug, to produce a first extract;

(d) assaying the first extract for activity of a protein encoded by the reporter gene;

(e) lysing a second culture of the cells containing the stably maintained DNA construct, which has been grown in the presence of the drug, to produce a second extract;

(f) assaying the second extract for activity of the protein encoded by the reporter gene; and (g) comparing the activities of the first extract and the second extract.

In the context of this disclosure, the term "promoter" or "promoter region" refers to a DNA sequence located upstream of (5' to) the coding sequence of a gene which controls the expression of the coding sequence by providing a recognition and binding site for RNA polymerase. The promoter region may include additional recognition or binding sites for other factors involved in the regulation of transcription of the gene. Certain promoters are constitutively expressed, whereas other promoters are inducible. An inducible promoter is not expressed, or only expressed at a relatively low level, in the absence of an inducer. In the presence of the inducer, the gene is "turned on" or the level of transcription increased. This is commonly mediated by the binding of a specific transcription factor (with or without bound drug) to a site included in the promoter, though other mechanisms are also possible.

In the context of this disclosure, the term "heterologous promoter" is defined as a promoter that does not naturally include a copy of the DRE. Useful heterologous promoters that can be used in a DNA construct according to the invention include, for example, the herpes simplex virus (HSV) thymidine kinase (TK) promoter, the SV40 early promoter and the Rous sarcoma virus (RSV) promoter. Other convenient heterologous promoters would be known to a person skilled in the art.

In the context of this disclosure, the term "reporter gene" refers to a gene encoding a protein that is easily assayed, wherein the assay provides a quantitative measure of the amount of protein (gene product) present. A first example of a useful reporter gene that can be used in a DNA construct according to the invention is the firefly luciferase gene. The protein encoded by this gene catalyzes a reaction that produces light as one of its reaction products. The amount of light emitted can be easily quantitated (*GeneLight*™ *Plasmids Technical Manual*, Promega) and correlates with the amount of luciferase protein present. A second example of a useful reporter gene according to the invention is the *E. coli* lacZ gene, which can be quantitated by a colorimetric assay (*GeneLight*™ *Plasmids Technical Manual*, Promega). A third example of a useful reporter gene according to the invention is the chloramphenicol acetyltransferase (CAT) gene. Here too, the reaction products of the CAT enzyme can be conveniently assayed to provide a quantitative measure of the amount of enzyme present [Gorman et al., *Mol. Cell. Biol.* 2: 1044–1051]. Other convenient reporter genes would be known to a person skilled in the art.

With regard to the third method of the invention described in general terms above, introduced DNA being "maintained" in cells should be understood as the introduced DNA continuing to be present in essentially all of the cells in question as they continue to grow and proliferate. That is, the introduced DNA is not diluted out of the majority of the cells over multiple rounds of cell division. Rather, it replicates during cell proliferation and at least one copy of the introduced DNA remains in almost every daughter cell. Introduced DNA may be maintained in cells in either of two fashions. First, it may integrate directly into the cell's genome. (This occurs at a rather low frequency.) Second, it may exist as an extrachromosomal element, or episome. In order for an episome not to be diluted out during cell proliferation, a selectable marker gene can be included in the introduced DNA and the cells grown under conditions where expression of the marker gene is required. Even in the case where the introduced DNA has integrated in the genome, a selectable marker gene may be included to prevent excision of the DNA from the chromosome. Examples of suitable marker genes are discussed in detail later in this disclosure.

In the examples described in detail below, DNA constructs according to the invention were introduced into hepatoma cells, in view of the fact that the human apo AI gene is expressed in liver cells. However, it may for some reason be desirable to practice the invention in a non-hepatic cell type, such as, for example, intestinal cells, in which the apo AI gene is also expressed [Gotto et al., *Methods Enzymol.* 128: 3–41 (1986)].

In the examples, the DNA constructs were introduced into cells by the calcium phosphate procedure of Gorman and co-workers [Gorman et al., *Mol. Cell. Biol.* 2: 1044–1051 (1982)]. However, a person skilled in the art would know alternative procedures for introducing DNA constructs into mammalian cells, such as, for example, retroviral infection and electroporation.

The induction of expression of a particular gene by a drug may occur according to one or more of a number of different mechanisms, as are known to persons skilled in the art:

1. The drug may bind directly to a cis-acting regulatory element of the gene, causing an increase in transcription of the gene.
2. The drug may bind to a transcription factor (protein or protein complex) that is already present in the cell in an inactive form, thus activating or derepressing it. The derepressed transcription factor may then be able to bind, generally with the drug, to a cis-acting regulatory element of the gene, consequently increasing transcription. Alternatively, binding of the drug to a transcription factor that is already present in the cytosol may cause its translocation to the nucleus. Once in the nucleus, the transcription factor (with or without bound drug, as the particular case may be) can interact with gene and increase transcription.
3. The drug may bind an inhibitor of the gene, rendering the inhibitor ineffective. For example, the inhibitor may be bound to a cis-acting repressor element, and binding of the drug to the inhibitor causes it to be released from the repressor element.
4. The drug may stabilize mRNA transcribed from the gene against degradation by the cellular machinery, thus lengthening its persistence in the cell and increasing the number of times it may be translated to protein.
5. The drug may cause increased synthesis of a transcription factor that positively regulates the gene. This may occur by any of mechanisms 1–4 operating on a second gene that encodes the transcription factor. Increased abundance of the transcription factor results in increased expression of the first gene, on which it acts.

The inventors have shown that the increase in the level of apo AI mRNA upon treatment of Hep3B and HepG2 cells with gemfibrozil is due primarily to increased rates of transcription of this gene. First, both in vitro nuclear run-off transcription assays (Example 5, FIG. 4) and transient transfection assays (Example 9, FIG. 8) indicated a significant two-fold increase in transcription of the apo AI gene in the presence of gemfibrozil. Second, as detailed in Example 2 below, when the cells were pretreated with actinomycin D, an inhibitor of RNA synthesis, the half-life of pre-existing apo AI mRNA was not significantly different in the presence or absence of gemfibrozil (Example 4, FIG. 3). That is, apo AI mRNA did not appear to be stabilized by gemfibrozil treatment. Taken together, these results indicate that the observed induction in apo AI mRNA level in response to gemfibrozil is mediated at the transcriptional level.

The inventors have also shown that the increase in apo AI transcription induced by gemfibrozil is mediated by the induction of transcription factors that interact with the DRE in the 5' flanking region of the apo AI gene in a sequence-specific manner. This was demonstrated in gel mobility-shift assays in which end-labeled apoAI-DRE DNA was incubated with a nuclear extract from Hep3B or HepG2 cells that had been treated with gemfibrozil and the reaction products were resolved by gel electrophoresis. Free DNA migrated rapidly, whereas DNA that was bound to protein factors was retarded (Examples 6 and 7, FIGS. 5 and 6).

Figure 6A:
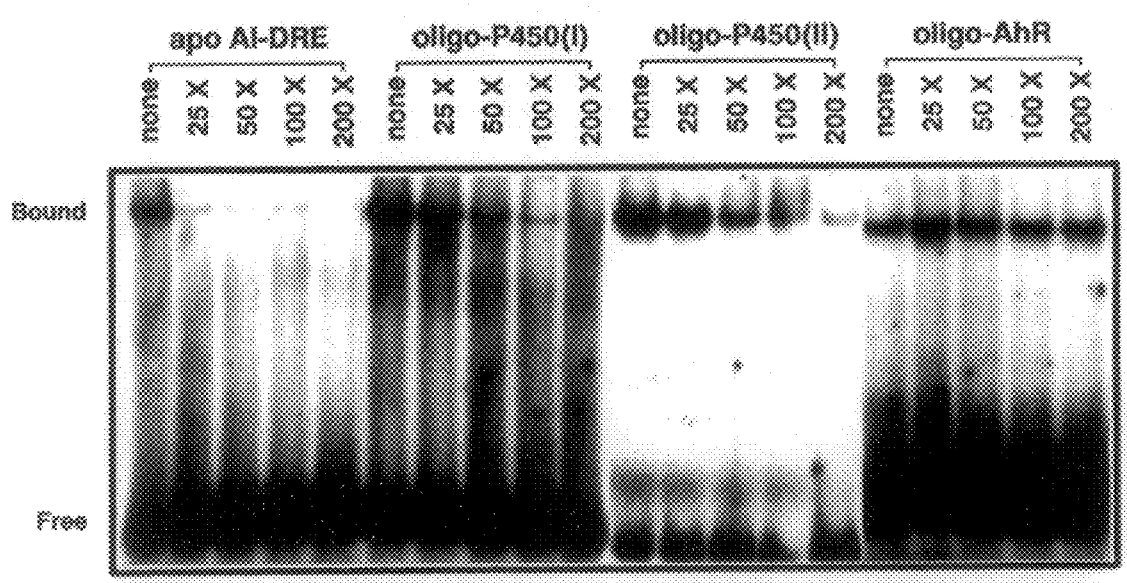
FIG. 6A shows an autoradiogram of a polyacrylamide gel used in competition gel mobility-shift assays involving $^{32}$P-oligo-apoAI-DRE, nuclear protein extract from Hep3B cells and excess competitor oligonucleotides oligo-apoAI-DRE (SEQ ID NO: 8), oligo-P450(I)(SEQ ID NO: 9), oligo-P450(II) (SEQ ID NO: 10) and oligo-AhR (SEQ ID NO: 14).
Figure 6B:
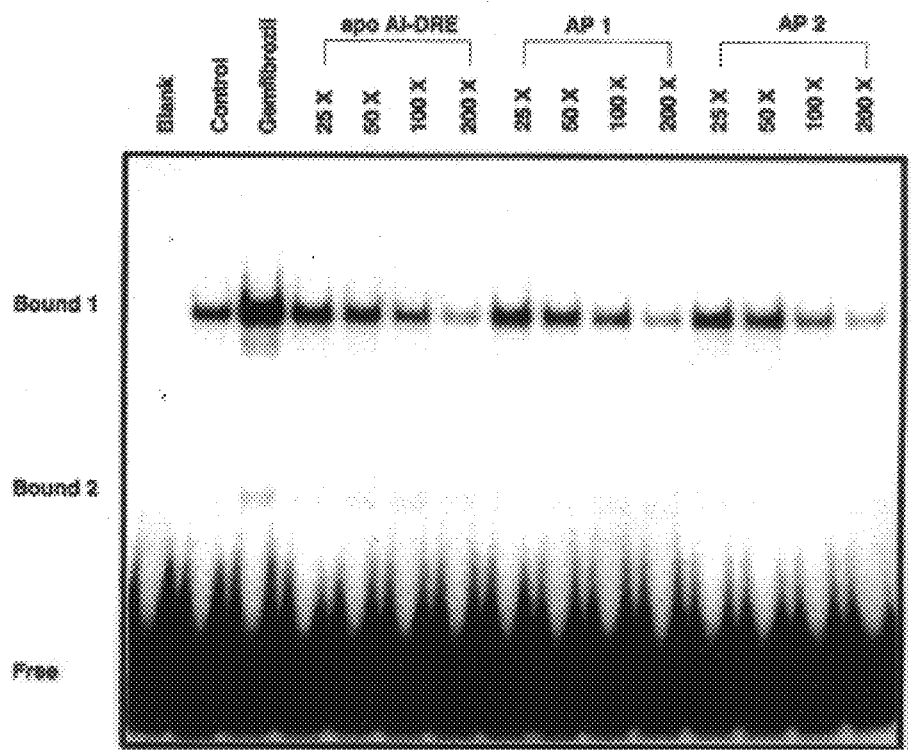
FIG. 6B shows an autoradiogram of a polyacrylamide gel used in competition gel mobility-shift assays involving $^{32}$P-oligo-apoAI-DRE, nuclear protein extract from Hep3B cells and excess competitor oligonucleotides oligo-apoAI-DRE, oligo-AP1 (SEQ ID NO: 11) and oligo-AP2(SEQ ID NO: 12).
Figure 6C:
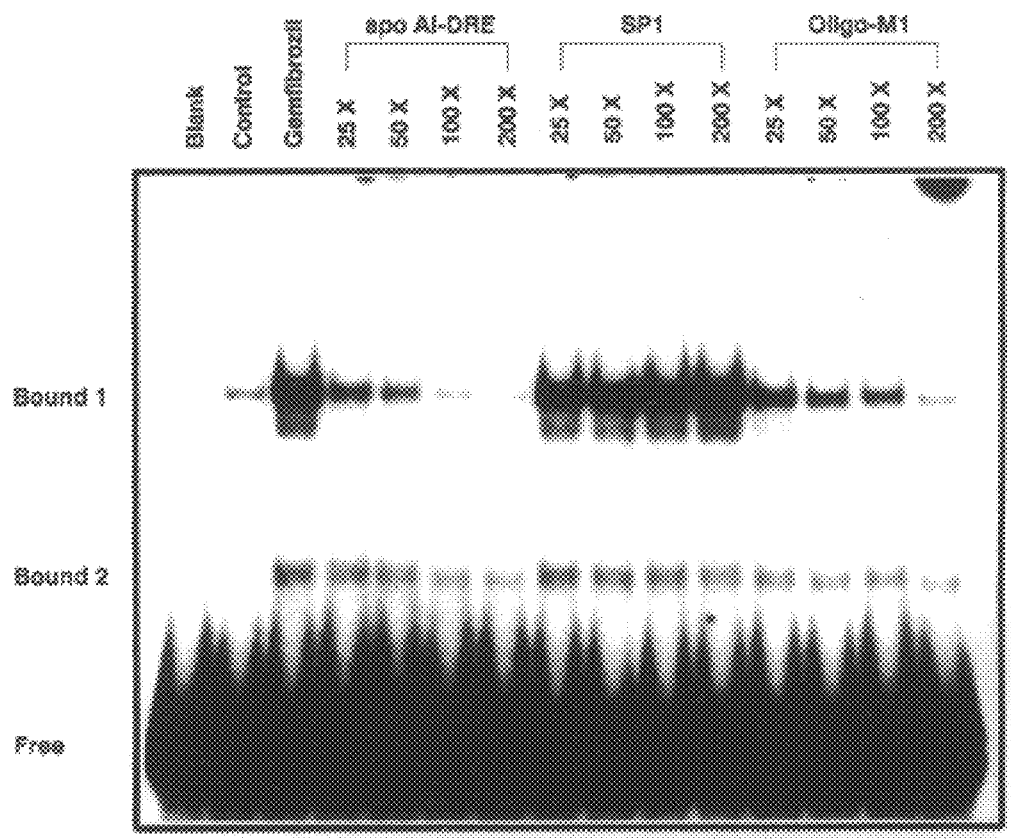
FIG. 6C shows an autoradiogram of a polyacrylamide gel used in competition gel mobility-shift assays involving $^{32}$P-oligo-apoAI-DRE, nuclear protein extracts from Hep3B cells and excess competitor oligonucleotides oligo-apoAI-DRE, oligo-SP1 (SEQ ID NO: 13) and oligo-M1 (mutated oligo-apoAI-DRE (SEQ ID NO:15))

In competition gel-mobility shift assays, excess unlabeled competitor DNA was included in the reaction mixture containing end-labeled apoAI-DRE DNA and Hep3B or HepG2 nuclear extract. In this type of assay, if the particular competitor DNA in a given reaction is able to bind strongly to the transcription factor(s), the observed level of the radiolabeled DNA-protein complex is reduced relative to a reaction without competitor DNA. Competition assays performed by the inventors are described in detail in Example 7 and the specific results are shown in FIG. 6. In summary, the results showed that nuclear factors induced by gemfibrozil bind apoAI-DRE in a highly sequence-specific manner. When the unlabeled competitor DNA was identical to the labeled DNA, competition was strong. In contrast, when the competitor DNA was identical except for a single nucleotide change in each of the two DRE, the efficiency of competition was reduced by 40%. Furthermore, when the competitor DNA was the DRE consensus sequence of CYP1A1 [P450(I) and (II)], competition was also strong. However, no competition was observed with a 200-fold molar excess of the GC-rich SP1 consensus sequence or the xenobiotic consensus sequence for the Ah receptor. These and the results of other competition assays are described in detail below.

The induction of specific nuclear proteins by gemfibrozil was also demonstrated by southwestern analysis. The results of these assays, including the apparent molecular weights and the relative abundance of the induced proteins are described in Example 8 and shown in FIG. 7. Using Scatchard analysis [Scatchard, *Ann. N.Y. Acad. Sci.* 51: 660–672 (1949)], the inventors have demonstrated that these nuclear proteins bind to the human apo AI-DRE with relatively high affinity in the nanomolar range (data not shown).

The functional role of the DRE in the induction of apo AI gene transcription by gemfibrozil was demonstrated in transient transfection assays using DNA constructs of the invention. Such assays are exemplary of how one could practice a method of the invention to screen for induction of apo AI gene expression by a candidate drug. As described in detail in Example 1, the inventors constructed plasmids derived from the pGL2-Basic Vector (Promega Inc.), which includes a luciferase reporter gene. In a first construct(SEQ ID NO:1), nucleotides −491 to +1 upstream from the transcription start site (+1) of the human apo AI gene, were linked upstream of the luciferase reporter gene and in a second construct (SEQ ID NO: 2), nucleotides −250 to +1 were so linked. Using these constructs, the first method of the invention described above was practiced. In each case, a significant two-fold increase in luciferase activity was observed for transfected cells that were grown in the presence of gemfibrozil, relative to transfected cells grown in the absence of this drug (Example 9, FIG. 8).

For a second set of exemplary assays, the inventors created DNA constructs according to the invention as described above in general terms. In plasmid pGL2 (apoAI-DRE) TK/luc (SEQ ID NO: 3), two copies of the DRE arranged in an imperfect inverted repeat with a spacer region interposed therebetween were linked upstream of the HSV TK promoter. This promoter was in turn functionally linked 5' to a luciferase reporter gene. In plasmid pGL2 (4×apoAI-DRE) TK/luc (SEQ ID NO: 4), four imperfect inverted repeats (eight DRE) were linked 5' to the HSV TK promoter. These DNA constructs were used to practice the second method of the invention outlined in general terms above. Cells into which construct pGL2 (apoAI-DRE) TK/luc was introduced demonstrated a significant two-fold increase in luciferase activity when grown in the presence of the drug. Cells transfected with pGL2 (4×apoAI-DRE) TK/luc displayed an additional 20–30% induction. These results show that the apo AI-DRE can confer drug-responsiveness on a heterologous promoter.

The third method described in general terms above provides another convenient way to screen for a drug that increases expression of the apo AI gene through the mediation of the DRE. In a prophetic example, a DNA construct according to the invention would be introduced into mammalian cells in culture by a method known to persons skilled in the art. The construct would include, functionally joined together in the 5'→3' direction of transcription, (I) at least one copy of a drug-responsive element (DRE) having at least about 80% homology with the DNA sequence 5'-G/C N T/G A/G GCTGGG-3', (ii) a heterologous promoter, (iii) a reporter gene and (iv) an untranslated region including a functional polyadenylation signal. Conveniently, the construct could also include an additional functional selectable marker gene whose expression is required under certain culture conditions to maintain the introduced DNA in the cells. For example, expression of the marker gene could provide resistance to hygromycin B [Wilson et al., *Plasmid* 33: 198–207 (1995)]. If the cells were consistently cultured in the presence of hygromycin B (Boehringer-Mannheim), only cells containing this marker gene would survive selection. Thus, the introduced DNA would be stably maintained in essentially all surviving cells. Similarly, if the marker gene coded for neomycin resistance [Colbere-Garapin et al., *J. Mol. Biol.* 150: 1–14 (1981)] and the cells were cultured in the presence of G418 [Geneticin, Life Technologies], the introduced DNA would be stably maintained. Other genes of this type, such as, for example, aminoglycoside phosphotransferase (APH) [Jimenz et al., *Nature* (*London*) 287: 869–871 (1980)] would be known to a person skilled in the art.

According to the invention, the stably transfected cell line would provide a convenient tool for screening candidate drugs. A culture of this cell line could be grown in the presence of the candidate drug, lysed and the lysate assayed for reporter gene activity. In parallel, a culture grown in the absence of the drug could be lysed and assayed. The assay results would then be compared to determine whether the drug increased reporter gene expression. The advantage of this third method is the convenience provided by not having to introduce a DNA construct transiently every time a candidate drug is screened.

It is important to note that the practice of the present invention for screening the drug gemfibrozil as described herein is the first demonstration of drug-induced protein-DNA interactions involved in the regulation of expression of the apo AI gene. The invention provides convenient DNA constructs, and convenient, rapid and efficient methods for screening for other drugs that may be involved in increasing expression of the apo AI gene through the mediation of the DRE.

The invention contemplates the assembly of a kit including reagents with which one could conveniently practice the invention. The kit would include a DNA construct as described herein, as well as a substrate of the reporter gene so that reporter gene activity could be quantitated. The invention also contemplates automation of the methods described herein. That is, a machine could be constructed that would practice the invention, further increasing convenience and efficiency.

Moreover, the invention permits the identification of transcription factors that bind to the DRE. A number of such factors are identified in Example 8 and FIG. 7. The invention additionally contemplates use of the DRE as a reagent for the purification of a transcription factor with which it interacts. For example, an oligonucleotide including the DRE could be conjugated to a resin to produce an affinity resin [de Wet et al., *DNA* 3: 437–447 (1984)]. A crude cell extract, such as a nuclear extract, could be incubated with the affinity resin under conditions where a transcription factor or factors would bind to the DRE moiety. After first washing the complexed resin to dissociate free and non-specifically bound proteins or protein complexes, a more stringent buffer would then be applied to elute specifically bound factors. This procedure could be performed using column chromatography or batchwise extraction as is known in the art.

All scientific publications cited herein are hereby incorporated by reference.

Although this invention is described in detail with reference to preferred embodiments thereof, these embodiments are offered to illustrate but not to limit the invention. It is possible to make other embodiments that employ the principles of the invention and that fall within its spirit and scope as defined by the claims appended hereto.

EXAMPLES

Example 1

Synthesis of Oligonucleotides and Construction of Plasmids

The synthetic oligonucleotides used in the examples described herein were synthesized using standard procedures on a Biosearch model 8600 DNA synthesizer at Core Facility for Protein/DNA Chemistry, Department of Biochemistry, Queen's University, Kingston, Ontario, Canada. DNA containing the human apo AI coding sequence (vector pKT218, ATCC No. 57024) was obtained from American Type Culture Collection, Rockville, Md. The nucleotide numbering scheme used below for this DNA sequence is identical to that used for GenBank accession no. M20656 (human apo AI).

Figure 2A:
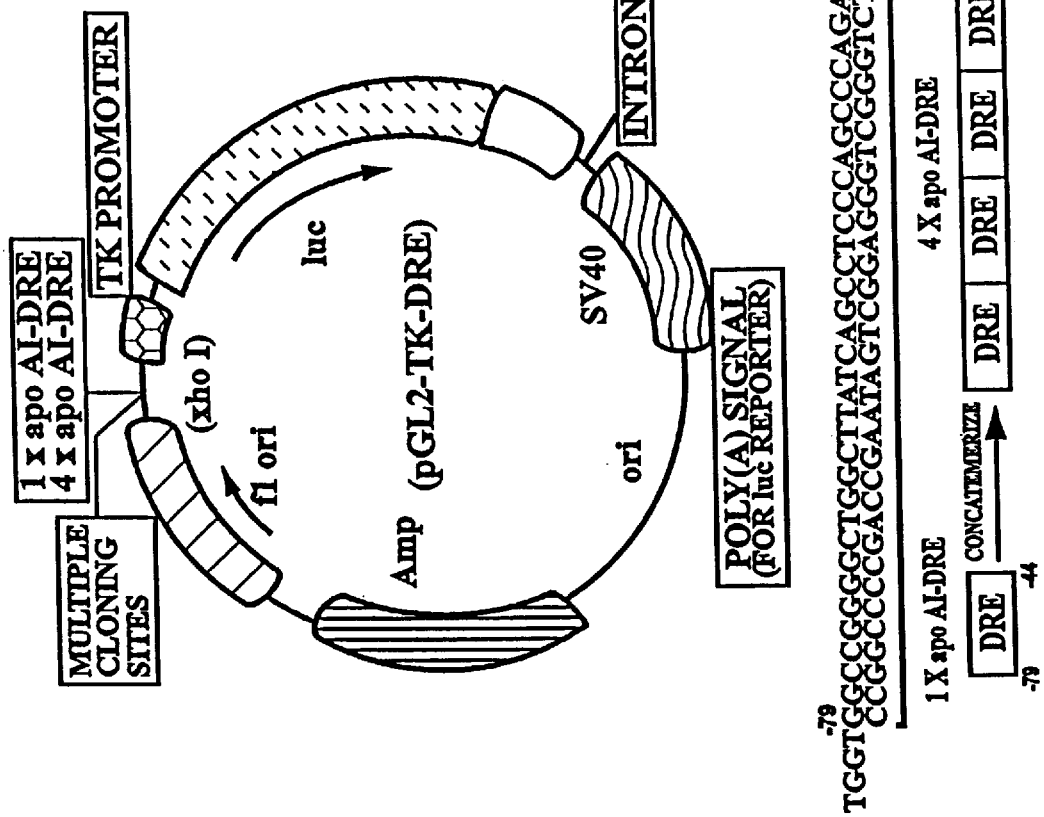
FIG. 2A, is a schematic diagram of plasmids pGL2 (apoAI-491)luc (SEQ ID NO: 1) and pGL2 (apo-AI-250)luc (SEQ ID NO: 2) according to the preferred embodiment of the invention.
Figure 2B:
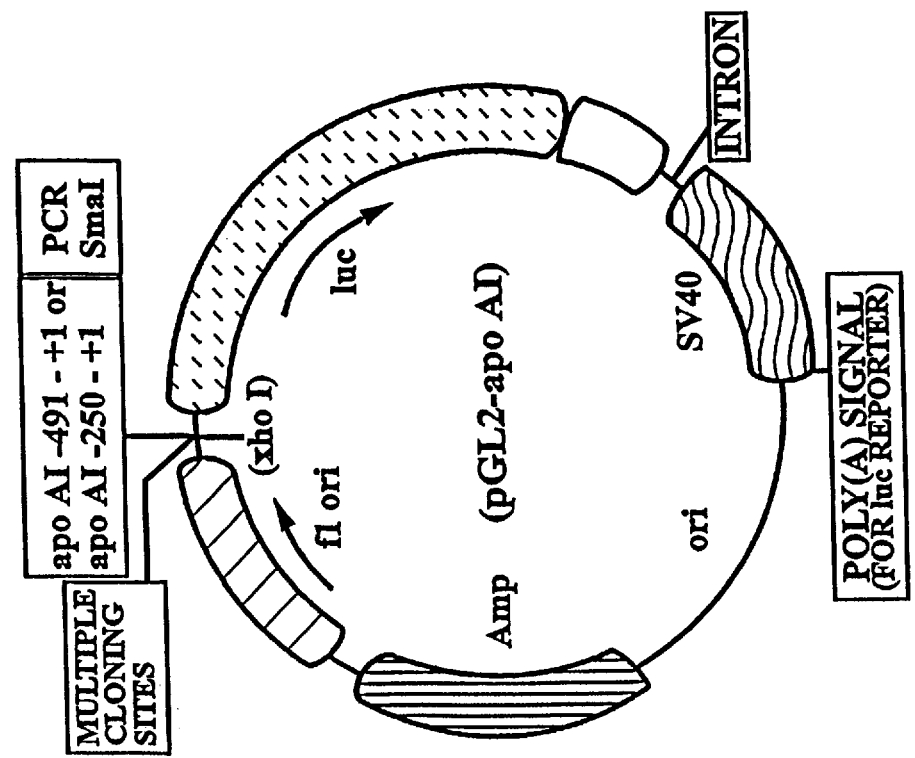
FIG. 2B is a schematic diagram of plasmids pGL2 (apoAI-DRE) TK/luc (SEQ ID NO: 3) pGL2 (4X apo-AI-DRE) TK/luc (SEQ ID NO: 4) according to the preferred embodiment of the invention.

Plasmid pGL2 (apoAI-491)luc (SEQ ID NO: 1) was constructed as follows: Two oligonucleotide primers complementary to the region upstream of the human apo AI gene between nucleotides −491 to −460 and between nucleotides −25 to +1, respectively, were synthesized. The two primers were mixed with high molecular weight genomic DNA from HepG2 cells and polymerase chain reaction (PCR) amplification was carried out under standard reaction conditions [PCR Protocols: A guide to methods and applications, Innis (ed.), Academic Press, San Diego, Calif. (1990); Sambrook et al., *Molecular Cloning: A laboratory Manual* (*2nd Edition*), Cold Spring Harbor Laboratory, Cold Spring Harbor, N.Y. (1989), 37]. The PCR protocol was 30 cycles of the following: 95° C. for 45 sec, 52° C. for 45 sec, and 72° C. for 30 sec. A 491 bp DNA fragment of the 5' flanking region of the human apo AI gene between nucleotides −491 to was generated, and its sequence was confirmed by DNA sequencing. The fragment was inserted into the XhoI site of the pGL2-Basic Vector (Promega Inc.), upstream of the luciferase reporter gene. The pGL2-Basic Vector includes, downstream of the luciferase gene, an untranslated region including a functional polyadenylation signal. Construct pGL2 (apoAI-491)luc is shown in FIG. 2, Panel A. Its sequence is given in the sequence listing appended hereto.

Plasmid pGL2 (apoAI-250)luc (SEQ ID NO: 2) was constructed by cleaving pGL2 (apo AI-491) with SmaI and releasing the DNA fragment extending from −491 to −251 upstream of the apo AI gene. The vector was gel purified and religated. This construct is also shown in FIG. 2, Panel A. Its sequence is given in the sequence listing appended hereto.

Plasmid pGL2 TK/luc (gift of Dr. M. Petkovich, Department of Biochemistry, Queen's University, Kingston, Ontario, Canada) was constructed by the insertion of the HSV thymidine kinase promoter upstream of the luciferase gene of the pGL2-Basic Vector at the Bg/II site.

Plasmid pGL2 (apoAI-DRE) TK/luc (SEQ ID NO: 3) was constructed by inserting a synthetic oligo-apoAI-DRE (between nucleotide positions −79 to −44 from the transcriptional start site of the apo AI gene) into the SmaI site of plasmid pGL2 TK/luc. This construct, carrying two copies of the DRE, is shown in FIG. 2, Panel B as "1×apoAI-DRE". Its sequence is given in the sequence listing appended hereto.

To construct related plasmid pGL2 (4×apoAI-DRE) TK/luc (SEQ ID NO: 4), also illustrated in FIG. 2, Panel B, four copies of the sticky-ended apo AI oligonucleotide depicted at the bottom of Panel B were ligated in tandem and inserted in the SmaI site of plasmid pGL2. Thus, this plasmid carries eight copies of the decanucleotide DRE. Its sequence is given in the sequence listing appended hereto.

Plasmid pGL2 (apo AI-mutant DRE) TK/luc was constructed by cloning a synthetic mutated oligo-apoAI-DRE 5'-GGC<u>ATTTTACTTA</u>TTATCAGCCT
<u>AAACTAAACTACC</u>-3' (SEQ ID NO: 17)into the SmaI site of pGL2 TK/luc.

The inserts in all of the above plasmids have the same 5'→3' orientation as found in the natural human apo AI 5' flanking region.

Example 2
Cell Culture and Drug Treatments

Human hepatoma cell lines, Hep3B and HepG2, were obtained from American Type Culture Collection (Rockville, Md.). Cells were grown in T75 flasks containing 20 ml of Eagle minimal essential medium (MEM) supplemented with 10% fetal bovine serum (FBS) as described previously [Tam, *Alcohol. Clin. Exp. Res.* 16: 1021–1028 (1992)]. Freshly confluent monolayers were washed twice with MEM and then incubated with fresh medium for 24 h in the presence of gemfibrozil, dissolved in ethanol, to give a final concentration of 40 $\mu$g/ml. Control cells were incubated with an equal volume (20 $\mu$l) of ethanol. In some examples, gemfibrozil and cycloheximide were added to the cells to give final concentrations of 40 $\mu$g/ml and 10 $\mu$g/ml, respectively. Where noted, Hep3B or HepG2 cells were also treated with actinomycin D, ranging from 0.625–10.0 $\mu$g/ml, in the presence or absence of gemfibrozil for various time periods as described. Cell viability was routinely monitored by trypan blue exclusion and lactate dehydrogenase leakage as described previously [Tam, *Alcohol. Clin. Exp. Res.* 16:1021–1028 (1992)]; the number of dead cells was not found to exceed 5% of the total number of cells.

Example 3
Quantification of Apolipoprotein AI mRNA Levels

The following procedure, which has been previously described by one of the inventors [Tam, *Atherosclerosis* 91: 51–61 (1991)], was used to quantitate the levels of apo AI mRNA in drug-treated and control cells: Total cellular RNA was isolated from HepG2 or Hep3B cells by extraction with guanidine-HCl. For Northern blotting, 20 $\mu$g of total RNA were denatured by treatment with glyoxal, subjected to electrophoresis on a 1.5% agarose gel and transferred to Zeta-probe GT membrane (Bio-Rad). Blots were prehybridized and hybridized with nick-translated apo AI and $\beta$-actin cDNA probes. $\beta$-actin was used as an internal control, since its cognate mRNA levels are not affected by gemfibrozil; other such control probes would be known to a person skilled in the art. All results were normalized using densitometric scans of Northern blots probed with radiolabeled $\beta$-actin to correct for loading variations.

Example 4
Analysis of Effect(s) of Gemfibrozil on Levels of apo AI mRNA

Previously, one of the inventors demonstrated that exposure of HepG2 and Hep3B cells to gemfibrozil results in a two-fold induction in apo AI mRNA levels [Tam, *Atherosclerosis* 91: 51–61 (1991)]. Elevation of apo AI mRNA levels by gemfibrozil or another drug could be accounted for by RNA stabilization and/or increased rates of transcription. The following protocols were used to determine which of these effects gemfibrozil produces, and a person skilled in the art would be able to use such protocols or variations thereof according to the invention to determine the nature of the effect of another drug on apo AI mRNA levels.

If gemfibrozil induces apo AI mRNA at the transcriptional level, then inhibition of RNA synthesis would be expected to affect such induction. To test this, Hep3B cells were treated both in the absence and presence of increasing amounts of actinomycin D, a known inhibitor of transcription, for 30 minutes prior to the addition of gemfibrozil. Actinomycin D at concentrations greater than or equal to 0.625 $\mu$g/ml were able to block the increase in apo AI mRNA levels that was observed when the cells were treated with gemfibrozil alone. Under the same regimen of drug treatment, similar results were obtained for HepG2 cells (data not shown). This constituted evidence that gemfibrozil is responsible for de novo induction of RNA synthesis.

Figure 3:
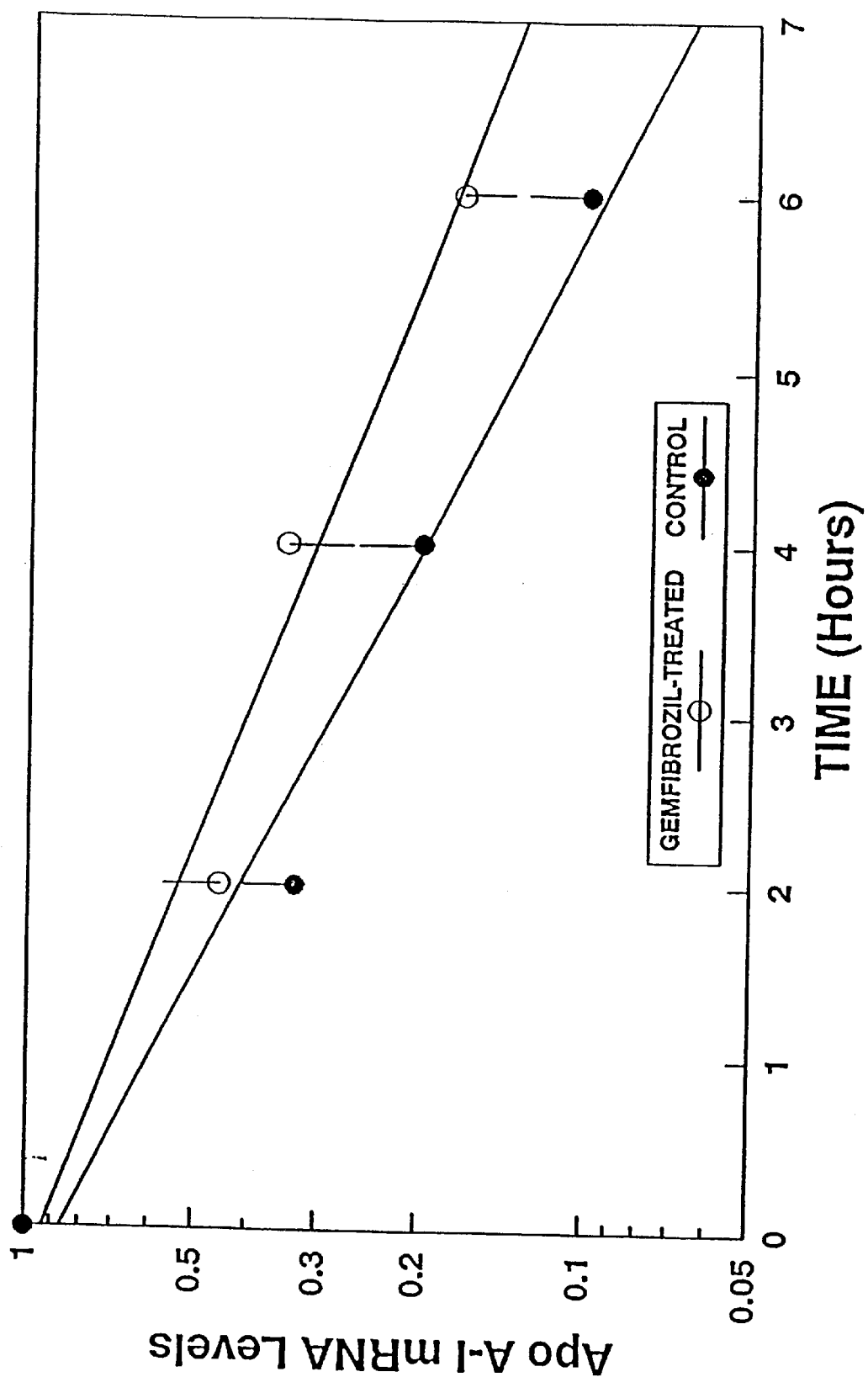
FIG. 3 is a graph showing the rates of degradation of apo AI mRNA in Hep3B cells cultured in the presence and absence of gemfibrozil.

In order to determine whether gemfibrozil is additionally responsible for the stabilization of apo AI mRNA, the half-lives of apo AI mRNA were compared for cells treated with gemfibrozil and untreated cells. Parallel cultures of newly confluent Hep3B cells were preincubated for at least 18 h in MEM +10% FBS in the absence or presence of gemfibrozil (40 $\mu$g/ml). The cells were then incubated with actinomycin D (1 $\mu$g/ml). RNA was isolated at 1, 2, 4 and 6 h later, and the levels of $\beta$-actin and apo AI mRNAs were determined by Northern analysis. Observed apo AI mRNA levels were normalized using densitometric scans of the same Northern blots probed with radiolabeled $\beta$-actin to correct for loading variations. The initial level of apo AI mRNA in the absence or presence of gemfibrozil was arbitrarily set at 1, and the results of the time course were plotted as shown in FIG. 3. Results are mean±S.E.M. of three trials.

Since addition of actinomycin D prevented further mRNA synthesis, this protocol provided that only apo AI mRNA present before the addition of actinomycin D could be detected. Thus, it was possible to determine from the decrease in apo AI mRNA over the time course, the rates at which it was degraded by the cellular machinery under the different treatment conditions. The half-lives determined for apo AI mRNAs following the addition of actinomycin D in the absence or presence of gemfibrozil were 1.7±0.4 h and 2.1±0.5 h, respectively, as shown in FIG. 3. These data were analyzed by the multivariate statistics and exact F statistics of the SAS (Statistical Analysis Systems) computer program. The analysis indicated that there was no significant difference ($P>0.05$) between the mRNA half-lives under the different culture conditions. Thus, it was concluded that gemfibrozil did not function to stabilize apo AI mRNA against degradation, but rather only induced its synthesis.

A person skilled in the art would be able to use the protocols similar to those outlined above to determine the nature of an effect produced by another drug on the levels of apo AI mRNA.

Example 5
Analysis of the Stimulation of Transcription by Gemfibrozil Treatment

The possibility that the transcription rate of the apo AI gene was elevated in response to gemfibrozil treatment was examined by nuclear run-off transcription assays. Nuclei ($2-3 \times 10^7$) were isolated from Hep3B cells cultured in the absence or presence of gemfibrozil (40 µg/ml) at 0, 2, 4, 10, 18, and 24 h. Preparation of the nuclei was according to the method described in Bartalena et al., *Mol. Endocrinol.* 6: 935–942 (1992). Isolated nuclei were resuspended in storage buffer (10 mM Tris-HCl, pH 7.5, 5 mM $MgCl_2$, 0.5 M D-sorbitol, 2.5% Ficoll, 50% glycerol, 10 mM spermidine, 20 mM DTT, 0.4 U/ml RNasin, 1 mM PMSF) at a concentration of $2-3 \times 10^8$ nuclei/ml and either used immediately or stored at $-70°$ C. until immediately before use.

In vitro nuclear run-off transcription assays were carried out as described [Bartalena et al., *Mol. Endocrinol.* 6: 935–942 (1992)] with minor modifications [Tam et al., *Atherosclerosis* 105: 235–243 (1994)]. Briefly, transcription was performed in a 400 µl reaction mixture containing 40 mM Tris-HCl, pH 8.3, 150 mM $NH_4Cl$, 7.5 mM $MgCl_2$, 0.62 mM ATP, 0.31 mM GTP and CTP, 100 µCi α-$^{32}$P-UTP (800 Ci/mmol), RNasin (80 U) and $3 \times 10^7$ nuclei. After incubation for 20 min at 26° C., unlabeled UTP was added to give a final concentration of 0.075 mM. The reaction was incubated further for 25 min at 26° C. Reactions were terminated by the addition of DNase I (RNase-free; Promega Inc.) and labeled RNA was isolated [Bartalena et al., *Mol. Endocrinol.* 6: 935–942 (1992)]. Total incorporation of label into RNA per assay ranged from $1 \times 10^7$ dpm to $5 \times 10^7$ dpm, all of which was used for a hybridization reaction.

Preparation of zeta-probe GT nylon filters was as outlined [Bartalena et al., *Mol. Endocrinol.* 6: 935–942 (1992)]. $^3$H-labeled control RNA was generated by performing standard in vitro transcription reactions using SP6 polymerase and vector pGEM 3Z (Promega). The newly synthesized $^{32}$P-labeled nuclear run-off products were hybridized to filter-bound plasmids containing an insert from the coding region of the human apo AI gene. The degree of nonspecific hybridization to the filters was determined in parallel using the control $^3$H-RNA. Hybridization, washing, and elution of bound, labeled RNA were carried out as described previously [McKnight et al., *J. Biol. Chem.* 254: 9050–9058 (1979)]. Quantitation of the bound RNA was by liquid scintillation counting.

Figure 4:
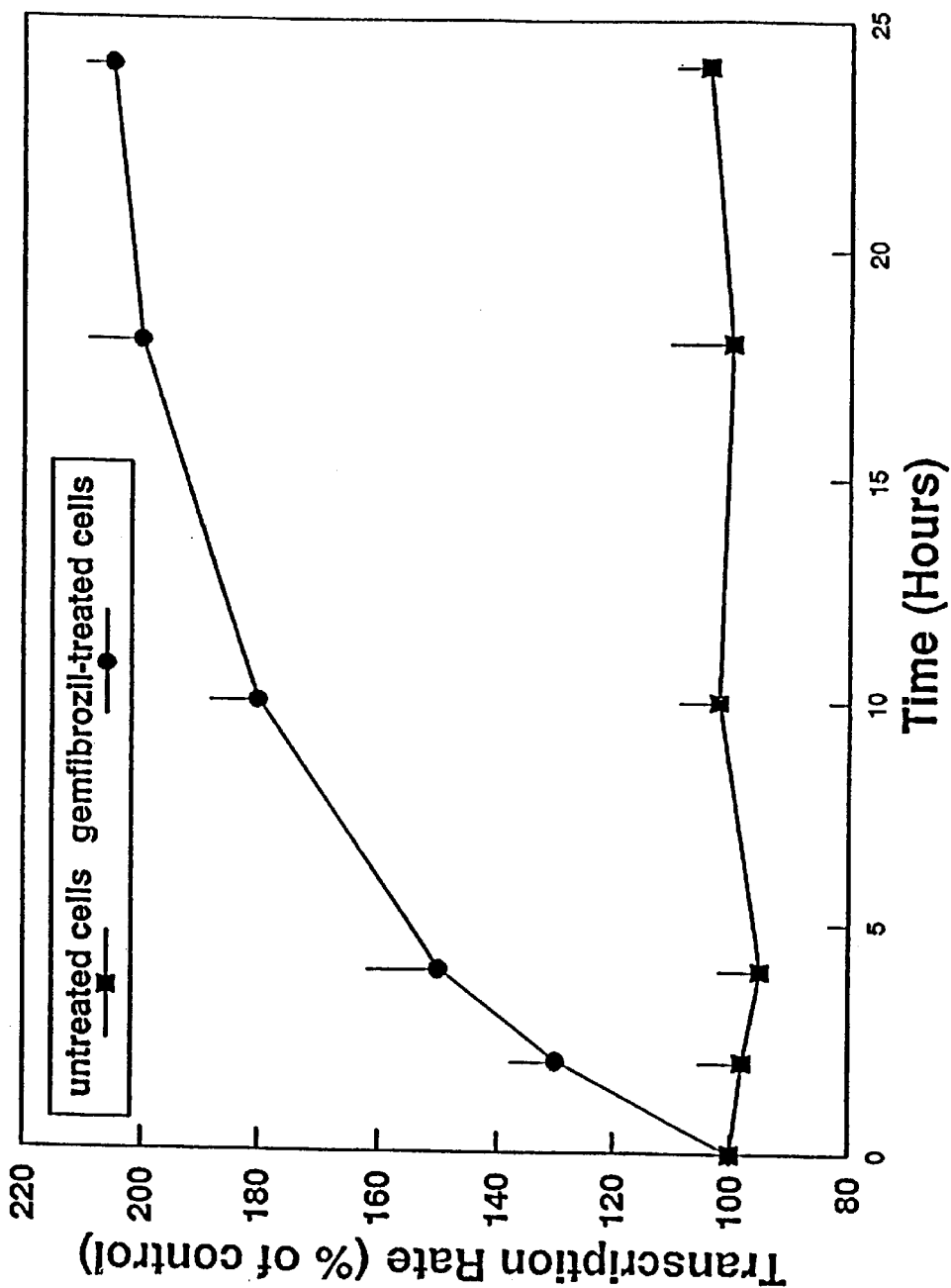
FIG. 4 is graph showing the rates of transcription of apo AI mRNA in Hep3B cells cultured in the presence and absence of gemfibrozil.

Relative transcription rates were calculated as part per million (ppm) /filter= (counts/min per filter–counts/min background)÷amount of [$^{32}$P] RNA used in hybridization (input count). These values were then normalized for hybridization efficiency as measured by binding of known amounts of $^3$H-labeled control RNA added to the hybridization mixture. This was then corrected for the size of the specific apo AI gene insert, as follows: ppm/gene=(ppm/filter+% hybridization)× (gene size+cDNA insert size). Sizes of the apo AI gene and apo AI cDNA fragments were 2 and 0.6 kilobases, respectively. The results of these assays, showing the effect of gemfibrozil on apo AI transcription rates at various times, are shown in FIG. 4. Results are mean±S.E.M. of three independent trials, expressed in percentage of the 0 h time point.

As shown in FIG. 4, the rate of transcription of the apo AI gene in Hep3B cells treated with gemfibrozil experienced a significant stimulation that was approximately two-fold at about 18 h. Maximal induction of apo AI transcription rate occurred between 18 and 24 h.

A person skilled in the art would be able to perform similar assays on other candidate drugs for stimulating apo AI expression to determine the nature of their effects on apo AI transcription rate.

Example 6
Interaction of Drug-inducible Nuclear Factors Isolated from Hepatoma Cells with the DREs of the Human apo AI Gene To investigate the possibility that the two-fold induction in apo AI transcriptional activity after gemfibrozil treatment involves protein-DNA interactions at the DREs located between nucleotides –76 to –46 relative to the transcription start site of the gene, gel mobility-shift assays were performed using proteins extracted from Hep3B or HepG2 nuclei.

Hep3B and HepG2 cells were grown as described above, and $3-6 \times 10^8$ cells were harvested to prepare nuclear extracts. Nuclear extracts were prepared by a modification of the method of Dignam and co-workers [Dignam et al., *Nucleic Acids Res.* 11: 1475–1489 (1983)]. All manipulations and centrifugations were performed at 4° C. When needed, phenyl-methyl-sulphonyl-fluoride (PMSF), dithiothreitol (DTT), aprotinin and leupeptin were added to the buffers just prior to use. Briefly, pelleted cells were suspended in two volumes of buffer A (10 mM HEPES, pH 8.0, 1.5 mM $MgCl_2$, 10 mM KCl, 0.5 mM DTT, 1 mM PMSF), and incubated on ice for 15 minutes. The swelled cells were then passed through a 23½G needle 5 times followed by a 26½G needle for another 5 strokes. Nuclei were obtained by centrifuging the cell lysate at 3300×g for 10 minutes. The pellets were resuspended in buffer B (10 mM HEPES, pH 8.0, 0.5 mM spermidine, 0.15 mM spermine, 1 mM EDTA, 0.25 mM EGTA, 50 mM KCl, 0.5 M sucrose, 0.5% Triton X-100, 1 mM DTT, 1 mM PMSF, 40 µg/ml aprotinin) and centrifuged at 6000×g for 10 min. This step was repeated twice. The crude nuclei were washed once with buffer C (same as buffer B except without Triton X-100). The resulting pellets were resuspended in ¼ pellet volume of Buffer D (20 mM HEPES, pH 8.0, 10% glycerol, 100 mM KCl, 2.0 mM $MgCl_2$, 0.2 mM EDTA), and then gently mixed with four volumes of buffer E (same as buffer D plus 0.5 M $(NH_4)_2SO_4$). After incubation on ice for 30 min, the suspensions were centrifuged at 50,000 rpm for 2 h in a TL 100.3 rotor in a Beckman benchtop ultracentrifuge. The collected supernatants were supplemented with $(NH_4)_2SO_4$ to a final concentration of 0.33 g/ml and incubated on ice for 30 min. After centrifugation at 20,000 rpm for 20 min in a TL 100.3 rotor, the nuclear extracts were dissolved in binding buffer (25 mM HEPES, pH 8.0, 12.5 mM $MgCl_2$, 20% glycerol, 50 mM KCl) and stored as aliquots at $-80°$ C. Nuclear protein content was determined by the method of Lowry and co-workers [Lowry et al., *J. Biol. Chem.* 193: 265–275 (1951)].

For the gel mobility-shift assays of this and the following example, nuclear extracts were incubated with 100 µg of poly (dI-dC) in binding buffer containing 5 mM DTT and 5

μM ZnCl$_2$ on ice for 30 min. Then, 2 fmoles (1×10$^4$ cpm) 5'-end-labeled synthetic oligonucleotide corresponding to the drug response element (DRE) or another element (as described in Example 7 and Table 1) were added to each reaction mixture. The reaction mixtures were incubated on ice for another 30 min. A 6% polyacrylamide gel was pre-electrophoresed at 80 V for 1 h. The samples were then loaded onto the gel and electrophoresed at 80 V for 4–6 h at 4° C. so as to resolve free DNA and protein-DNA complexes. The gel buffer for Example 6, FIG. 5 was 10 mM Tris-HCl, 5 mM sodium acetate, 2.5 mM EDTA, pH 7.2. The gel buffer for Example 7, FIG. 6 was 0.5×TBE (44.5 mM Tris-HCl, 44.5 mM boric acid, 1 mM EDTA, pH 7.2). The gel was vacuum-dried and exposed to Kodak x-ray film at 80° C. with a DuPont Hi-plus intensity screen. A band representing a protein-DNA complex was identified by autoradiography, excised from the gel, and quantitated by Cerenkov counting.

Figure 5:
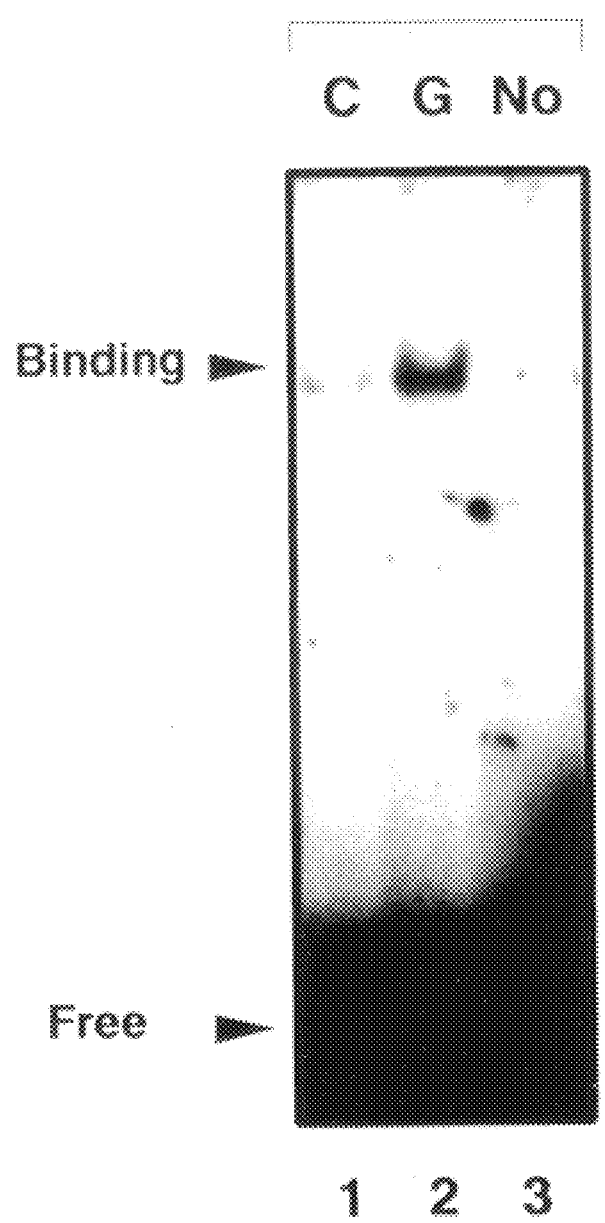
FIG. 5 shows an autoradiogram of a polyacrylamide gel used in gel mobility-shift assays involving $^{32}$P-oligo-apoAI-DRE and nuclear protein extracts from Hep3B cells cultured in the presence and absence of gemfibrozil.

A double-stranded synthetic oligonucleotide, designated oligo-apoAI-DRE, corresponding to the apo AI promoter region between nucleotides −79 to −44 (5'-GGCCGGGGCTGGCTTATCAGCCTCCCAGCCCAGA-CC-3'); SEQ ID NO: 8was 5'-end-labeled with $^{32}$P and incubated with nuclear extract proteins from hepatoma cells with and without gemfibrozil treatment under the reaction conditions described above. As shown in FIG. 5, in the absence of nuclear extract, labeled oligo-apoAI-DRE migrated to the bottom of the gel (lane 3, "no protein", lower arrow). In contrast, a more slowly migrating $^{32}$P-oligo-apoAI-DRE complex was evident in reactions where the oligonucleotide was incubated with extract prepared from Hep3B cells (lane 1, "C", upper arrow). In reactions where the nuclear extract was derived from Hep3B cells treated with gemfibrozil, the amount of this complex was significantly higher (lane 2, "G"). Similar results were obtained for HepG2 cells.

When the same type of gel mobility-shift assays were performed using nuclei from gemfibrozil-treated hepatoma cells that had also been treated with cycloheximide, a known inhibitor of protein synthesis, induction of the oligo-apoAI-DRE-protein complex was not seen (data not shown). This result was taken as evidence that gemfibrozil induces de novo synthesis of the nuclear proteins that bind oligo-apoAI-DRE to form the protein-DNA complex of the assay.

Example 7
Competition Gel Mobility-shift Studies

In order to determine the specificity of binding of the drug-inducible nuclear proteins to oligo-apoAI-DRE (SEQ ID NO: 8), competition gel mobility-shift assays were performed in which several different unlabeled synthetic double-stranded oligonucleotides were added to reaction mixtures such as those described above, to study their ability to compete against oligo-apoAI-DRE in binding to the nuclear factors. The synthetic oligonucleotides (SEQ ID NOS: 8–15) used as competitors are identified in Table 1. In each of these assays, the amount of nuclear proteins was held constant at 5 μg and the amount of labeled oligo-apoAI-DRE was held constant at 25 ng. Various amounts of unlabeled competitor oligonucleotide were added to the reaction mixture 15 min prior to the addition of labeled oligo-apoAI-DRE DNA. The labels in FIG. 6 indicate the degree of molar excess of the particular competitor DNA, relative to the concentration of oligo-apoAI-DRE DNA. The bands representing specific protein-DNA complexes (indicated in FIG. 6 as "bound 1") were identified by autoradiography, excised from the gel, and quantitated by Cerenkov counting. Non-specific-protein-DNA complexes and free labeled oligonucleotide are indicated in FIG. 6 as "bound 2" and "free", respectively. (It should be noted that the "bound 2" complex does not appear in FIG. 5 because of the different gel buffer used.) $^{32}$P-labeled oligo-apoAI-DRE was also incubated with no protein ("blank") or with nuclear extracts from control Hep3B or HepG2 cells ("control", Panels B and C).

As shown in Panels A, B and C of FIG. 6, binding of labeled oligo-apoAI-DRE to the nuclear extract from gemfibrozil-treated Hep3B cells was efficiently blocked by competition with a 50- to 100-fold molar excess of unlabeled oligo-apoAI-DRE. As shown in Panel C and the last line of Table 1, the efficiency of such competition was reduced by 40% when a mutated oligo-apoAI-DRE (oligo-M1) having two (G→A) transitions at nucleotides −72 and −69 within the DRE motif was used as the competitor DNA. In separate methylation interference assays (data not shown), nucleotides −72 and −69 were shown to be included in the contact points of protein factors bound to the DRE.

Table 1 also summarizes the results of other competition assays. The DNA fragments [(P450(I) and (II)] of the CYP1A1 gene [Sogawa et al., Proc. Natl. Acad. Sci. USA 83: 8044–8048 (1986)], which contain a DNA sequence very similar to apoAI-DRE, were found to compete efficiently with labeled oligo-apoAI-DRE in binding to the nuclear factor(s), as shown in FIG. 6, Panel A. Furthermore, the AP1 and AP2 consensus binding elements [Faisst et al., Nucleic Acids Res. 20: 3–26 (1992)] were also able to compete efficiently with oligo-apoAI-DRE, as shown in FIG. 6, Panel B. However, no competition was observed with a 200-fold molar excess of the GC-rich, SP1 consensus sequence [Faisst et al., Nucleic Acids Res. 20: 3–26 (1992)] (FIG. 6, Panel C), nor with the core recognition motif of the Ah receptor [Whitlock, Jr., Annu. Rev. Pharmacol. Toxicol. 30: 251–277 (1990); Fujisawa-Sehara et al., Proc. Natl. Acad. Sci. USA 85: 5859–5863 (1988)] (FIG. 6, (Panel A).

Example 8
Southwestern Blot Analyses

To characterize further the nuclear factors that bind to oligo-apoAI-DRE, southwestern analyses were carried out. Briefly, samples of nuclear extract from Hep3B cells with and without gemfibrozil treatment were mixed with an equal volume of sample buffer (5% SDS, 5 mM Tris-HCl, pH 6.8, 200 mM DTT, 20% glycerol, 0.5% pyronin Y) and subjected to electrophoresis on a 10% SDS-polyacrylamide gel at room temperature. Protein samples on the gel were electrotransferred to a Millipore immunobilon-P membrane in 25 mM Tris-HCl, 192 mM glycine, 20% (v/v) methanol, and 0.002% SDS at room temperature for 4 h. Hybridization of 5'-end-labeled oligonucleotides to the proteins immobilized on the membrane was performed according to the method of Singh and co-workers [Singh et al., Biotechniques 7: 252–261 (1989)].

Figure 7:
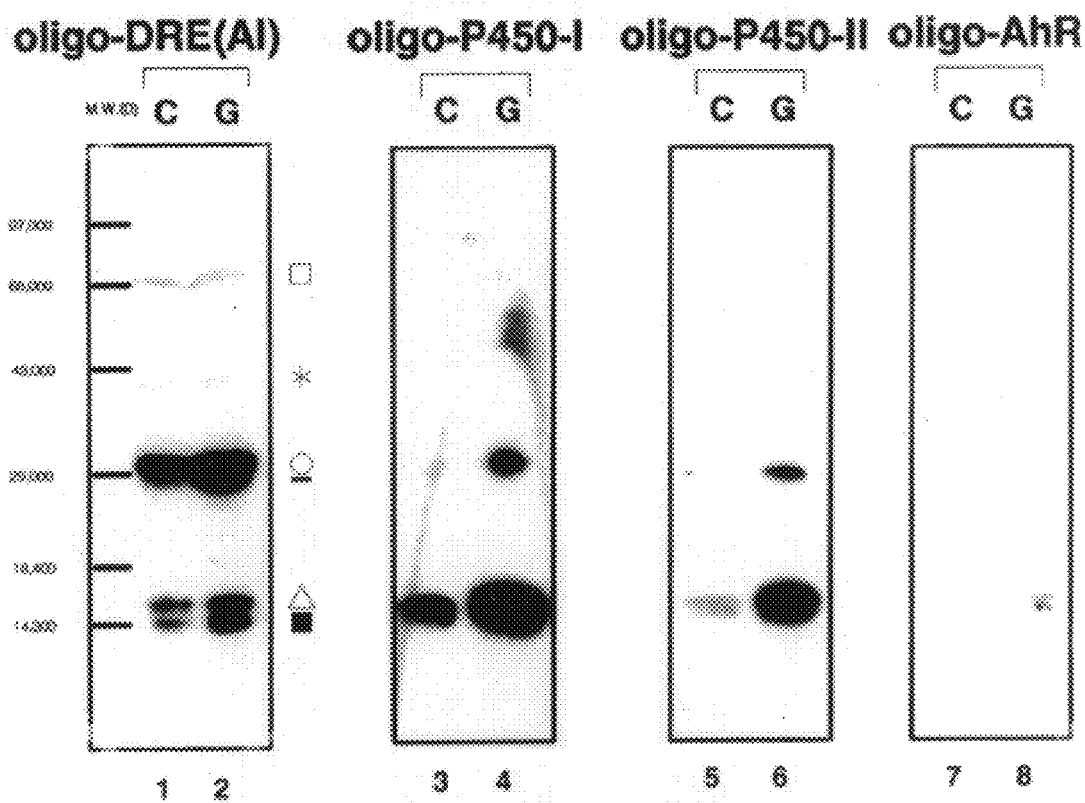
FIG. 7 shows autoradiograms of southwestern blots used in binding assays involving nuclear protein extracts from Hep3B cells probed with $^{32}$P-oligo-apoAI-DRE, $^{32}$P-oligo-P450(I), $^{32}$P-oligo-P450(11) and $^{32}$P-oligo-AhR.

The electrotransferred nuclear proteins on the membrane were probed with $^{32}$P-labeled oligo-apoAI-DRE, and the results are shown in FIG. 7, lanes 1 and 2. Molecular weight markers are indicated by solid lines beside lane 1. As indicated by a solid horizontal bar beside lane 2, labeled oligo-apoAI-DRE bound to a protein band of approximately 28 kDa in size. This band appeared to be inducible by gemfibrozil treatment since no such band was detectable in similar assays performed with nuclear proteins extracted from control cells (lane 1). Oligo-apoAI-DRE also bound to several proteins that were present in both gemfibrozil-treated and untreated samples. Two of these proteins have apparent molecular weights of approximately 68 kDa and 42 kDa, indicated in FIG. 7 by an open square and a star, respectively. These two protein bands gave signals of similar intensity on the autoradiograph, and were therefore used as internal controls for protein loading. In addition, three other protein bands with apparent molecular weights of approximately 30 kDa (open circle), 15 kDa (open triangle) and 14.5 kDa (solid square) were induced by gemfibrozil treatment.

In order to determine the specificity of binding of these drug-inducible protein bands to oligo-apoAI-DRE, separate southwestern blot analyses were performed using the following $^{32}$P-labeled oligonucleotides, which were described and referenced in Example 7: oligo-P450 (I), oligo-P450 (II), and oligo-AhR. As had been observed for oligo-apoAI-DRE, two protein bands with apparent molecular weights of approximately 30 kDa and 15 kDa were found to bind to $^{32}$P-oligo-P450 (I) (FIG. 7, lanes 3 and 4) and $^{32}$P-oligo-P450 (II) (FIG. 7, lanes 5 and 6). Furthermore, these two bands were highly inducible upon gemfibrozil treatment. In contrast, no nuclear proteins from control and gemfibrozil-treated cells interacted with $^{32}$P-oligo-AhR (FIG. 7, lanes 7 and 8). Similar results were observed in three separate studies. These data indicate that the drug-inducible protein bands bound specifically to the DRE consensus sequence.

Example 9
Functional Analysis of apoAI-DRE

To analyze the role of apoAI-DRE in the regulation of human apo AI gene expression in response to gemfibrozil, i.e., to show that the DRE was able to confer responsiveness to gemfibrozil, transient transfection assays were carried out using a series of pGL2-derived luciferase reporter plasmids, the construction of which was described in Example 1.

The assays were performed according to the following protocol: HepG2 or Hep3B cells were maintained as monolayers on 100 mm plates in MEM supplemented with 10% FBS. Transient DNA transfections were performed by the calcium phosphate precipitation procedure described by Gorman and co-workers [Gorman et al., *Mol. Cell. Biol.* 2: 1044–1051 (1982)]. Ten µg of total DNA was used per plate, including 4 µg of pGL2-derived luciferase reporter DNA and 6 µg of carrier pGL2 Basic Vector. After glycerol shock, the cells were washed twice with phosphate-buffered saline (PBS) and once with MEM and cultured in MEM plus 10% FBS in the absence or presence of gemfibrozil (40 µg/ml) for 24 h with changes of fresh medium.

Transfected cells were harvested and assayed for luciferase activity as described in the *GeneLight™ Plasmids Technical Manual*, Promega Corporation, WI, pp. 1–39 (1991). Briefly, the cells were washed three times in PBS, and then incubated for 10 min with 125 µl of 1×luciferase cell culture lysis buffer (Promega). The plates were scraped, the lysates were transferred to microfuge tubes, and the samples were centrifuged for 5 min in a microfuge. The resulting supernatants were assayed immediately or stored at −70° C. until used. In the luciferase assay, aliquots of supernatant were mixed with 100 µl of 1×luciferase assay substrate (Promega) in a test tube at room temperature, and light output (mV) was measured for 10 sec using a 1250 LKB luminometer. All luciferase activities are reported as mean±S.E.M. Significance of group differences was determined by the student t-test, using two-tailed P values.

In all transfections, 5 µg of an internal control plasmid (pSG Δ Lac Z), containing the *E. coli* lacZ gene under the control of the SV40 early promoter and enhancer, were co-transfected with the reporter plasmid in order to correct for differences in transfection and harvesting efficiency. Transfected cells were harvested as described above and β-galactosidase activities in the cell lysates were determined [*GeneLight™ Plasmids Technical Manual*, Promega Corporation, Wisconsin, pp. 1–39 (1991)]. The pGL2—Promoter Vector (Promega), which contains an SV40 promoter, was used as a reference for both transfection and luciferase assays.

Figure 8:
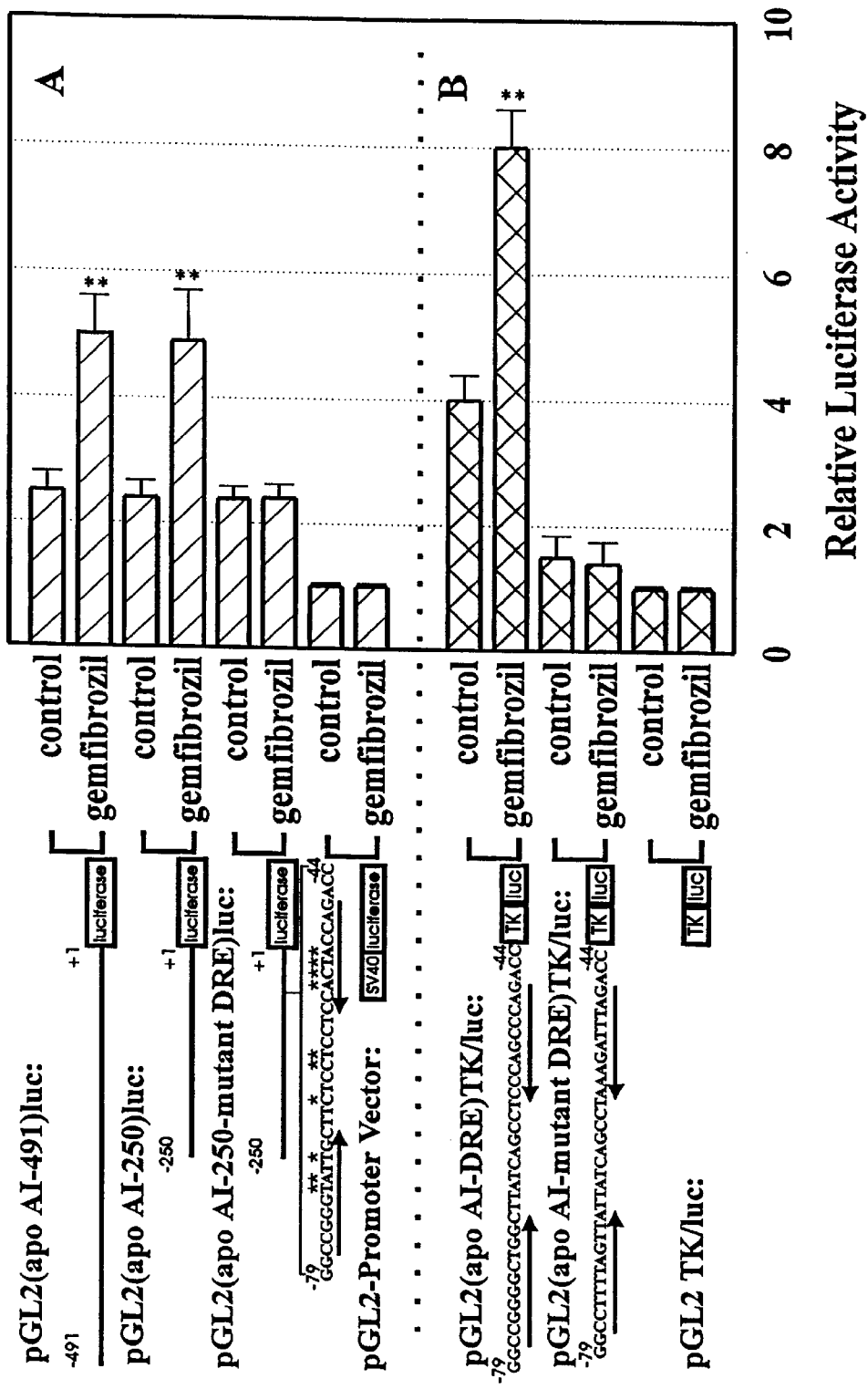
FIGS. 8A and 8B are schematic representations of pGL2-apoAI and pGL2-apoAI-DRE TK/luciferase reporter gene constructs and corresponding luciferase activity in transfected Hep3B cells.

Panel A of FIG. 8 concerns assays conducted with plasmids in which the SV40 early promoter was inserted upstream of the luciferase reporter gene of the pGL2 vector, and a portion of the 5' flanking region of the human apo AI gene was inserted upstream of this heterologous promoter. (The construction of these plasmids was outlined in Example 1.) The left side of Panel A is a schematic diagram of each plasmid's construction, and the right side is a bar graph of the level of luciferase activity in cells transfected in the absence (control) or presence of gemfibrozil. Luciferase activities of the constructs are expressed relative to that of pGL2-Promoter Vector. In both Panels A and B, results are mean±S.E.M. for six independent trials, each of which was carried out in triplicate. ** Significantly different from control (p<0.001, two-tail t test).

Control plasmid pGL2-Promoter Vector, containing the SV40 early promoter but no apo AI 5' sequence, exhibited the same level of luciferase activity in the absence and presence of gemfibrozil. In contrast, both plasmid pGL2 (apoAI-491) luc(SEQ ID NO: 1) and plasmid pGL2 (apoAI-250)luc (SEQ ID NO: 2)showed a significant two-fold induction of luciferase activity in the presence of gemfibrozil.

Panel B of FIG. 8 shows the results of assays conducted with plasmids in which the HSV TK promoter was inserted upstream of the luciferase reporter gene of the pGL2 vector, and various oligonucleotides containing the human apo AI gene DRE were inserted upstream of this heterologous promoter. (The construction of these plasmids was outlined in Example 1.) The left side of Panel B is a schematic diagram of each plasmid's construction, and the right side is a bar graph of the level of luciferase activity in cells transfected in the absence (control) or presence of gemfibrozil. Luciferase activities of the constructs are expressed relative to that of pGL2 TK/luc.

The control vector pGL2TK/luc demonstrated no change in level of luciferase activity in response to gemfibrozil treatment. In transient transfection assays in the absence of gemfibrozil, cells transfected with pGL2 (apoAI-DRE) TK/luc (SEQ ID NO: 3) containing two copies of the decanucleotide DRE exhibited approximately four-fold higher luciferase activity than cells transfected with the control vector pGL2 TK/luc. This suggests that the DRE can act as an enhancer that can increase expression of the reporter gene. Furthermore, the luciferase activity of pGL2 (apoAI-DRE)TK/luc was increased by an additional two-fold in the presence of gemfibrozil. The same assays were performed with plasmid pGL2(4×apoAI-DRE)TK/luc (SEQ ID NO: 4)(data not shown). This plasmid appeared to be both a better enhancer than pGL2 (apoAI-DRE)TK/luc in the absence of gemfibrozil, and a better inducer than pGL2 (apoAI-DRE)TK/luc in the presence of gemfibrozil, by a factor of about 20–30%.

The same assays were also performed with plasmid pGL2(apoAI-mutant DRE)TK/luc, which is based on plasmid pGL2 (apoAI-DRE)TK/luc but contains the following mutations: in the 5' DRE (C(-76)→A), (G(-75)→T), (G(-74)→T), (G(-73)→T), (G(-72)→T), (C(-71)→A), (T(-70)→C), (G(-69)→T), (G(-68)→T) and (C(-67)→A); in the 3' DRE (C(-55)→A), (C(-54)→A), (C(-53)→A), (A(-52)→C), (G(-51)→T), (C(-50)→A), (C(-49)→A), (C(-48)→A), (A(-47)→C) and (G(-46)→T). (The sequence containing these mutations(SEQ ID NO: 17) is given in Example 1.) As shown in FIG. 8, Panel B, plasmid pGL2(apoAI-mutant DRE)TK/luc had lost both the apparent enhancer ability and responsiveness to gemfibrozil treatment.

TABLE 1

Nucleotide sequences of oligomers used for competition gel mobility-shift studies

| Designation of oligomer and SEQ ID No. | Features of oligomer | Sequence of oligomer | Competition efficiency[a] |
|---|---|---|---|
| apoAI-DRE (SEQ ID No: 8) | Drug response element (DRE) of the human apo AI gene | 5'-GGCCGGGGCTGGCTTATC AGCCTCCCAGCCCAGACC-3' | 100 |
| P450(I) (SEQ ID No: 9) | DRE consensus sequence of CYP1A1 | 5'-CACAGGGGCTGGGGAG-3' | 95 ± 3 |
| P450(II) (SEQ ID No: 10) | DRE consensus sequence of CYP1A1 | 5'-GACCCCAGCCTTCACA-3' | 96 ± 4 |
| AP1 (SEQ ID No: 11) | AP1 consensus binding element | 5'-GCAGTCACAGTGACT CAGCAGAATCT-3' | 100 ± 5 |
| AP2 (SEQ ID No: 12) | AP2 consensus binding element | 5'-GATCGAACTGACCGCCCG CGGCCCGT-3' | 98 ± 3 |
| SP1 (SEQ ID No: 13) | SP1 consensus binding element | 5'-CTGCGGGGCGGGGCAGA-3' | 0 |
| oligo-AhR (SEQ ID No: 14) | Xenobiotic response element at which the aryl hydrocarbon (Ah) receptor is known to bind | 5'-AGTTGCGTGAGAAGA-3' | 0 |
| oligo-M1 (SEQ ID No: 15) | Mutated apoAI-DRE | 5'-TGGTGGCCGGGACTAGC TTATGGT-3' | 60 ± 5 | a: The specificity of the drug-inducible nucelar proteins toward the labeled oligo-apoAI-DRE was determined by comparative competition experiments using various unlabeled synthetic oligomers. The competition efficiency was arbitrarily set at 100 for unlabeled apoAI-DRE. Results are the mean ± S.E.M. of three separate experiments. Mutated nucleotides (G → A) in the mutated apoAI-DRE are indicated by an asterisk (*). The consensus sequences for various elements are underlined.

What is claimed is:

1. A method of screening for a drug that increases expression of a gene for apolipoprotein AI (apo AI), comprising the steps of:

growing in the absence of a drug a first culture of mammalian cells comprising a DNA construct consisting of, functionally joined together in the 5'–3' direction of transcription, (i) at least one copy of a drug-responsive element (DRE) having DNA sequence 5'-G/C N T/G A/G GCTGGG-3' (SEQ ID No: 5) or its complement, (ii) a heterologous promoter, (iii) a reporter gene and (iv) an untranslated region including a functional polyadenylation signal;

lysing the first culture to produce a first extract;

assaying the first extract for activity of a protein encoded by the reporter gene;

growing a second culture of said cells in the presence of said drug;

lysing the second culture to produce a second extract;

assaying the second extract for activity of said protein encoded by the reporter gene; and comparing the activities of the first extract and the second extract;

wherein an increase of the activity of the second extract as compared to the first extract is indicative of a drug that increases expression of a gene for apolipoprotein AI (apo AI).

2. The method of claim 1, wherein said DNA construct includes at least two copies of said DRE or its complement.

3. The method of claim 2, wherein the two copies of the DRE or its complement are arranged as an inverted repeat relative to each other.

4. The method of claim 3, wherein a spacer DNA region of about 10 nucleotides is interposed between the two copies of the DRE or its complement.

5. The method of claim 3, wherein the reporter gene is the firefly luciferase gene.

6. The method of claim 3, wherein the reporter gene is the *E. coli* lacZ gene.

7. The method of claim 3, wherein the heterologous promoter is the herpes simplex virus thymidine kinase promoter.

8. The method of claim 3, wherein the heterologous promoter is the SV40 early promoter.

9. The method of claim 3, wherein at least one copy of the DRE has the sequence 5'-CGGGGCTGGC-3' (SEQ ID No: 6).

10. The method of claim 3, wherein at least one copy of the DRE has the sequence 5'-CTGGGCTGGG-3' (SEQ ID No: 7).

11. The method of claim 1, wherein said construct is contained in a vector.

12. The method of claim 11, wherein said vector containing said construct is plasmid pGL2 (apoAI-DRE) TK/luc (SEQ ID NO: 3).

13. The method of claim 11, wherein said vector containing said construct is plasmid pGL2 (4× apoAI-DRE) TK/luc (SEQ ID No: 4).

14. A method of screening for a drug that increases expression of a gene for apolipoprotein AI (apo AI), comprising the steps of:

growing in the absence of a drug a first culture of mammalian cells comprising a DNA construct consisting of, functionally joined together in the 5'→3' direction of transcription, (i) at least one copy of a drug-responsive element (DRE) having DNA sequence 5'-G/C N T/G A/G GCTGGG-3' (SEQ ID No: 5) or its complement, (ii) a heterologous promoter, (iii) a reporter gene and (iv) an untranslated region including a functional polyadenylation signal;

wherein said DNA construct is stably maintained in the cells;

lysing the first culture to produce a first extract;

assaying the first extract for activity of a protein encoded by the reporter gene;

growing a second culture of said cells comprising said stably maintained DNA construct in the presence of the drug;

lysing the second culture to produce a second extract;

assaying the second extract for activity of said protein encoded by the reporter gene; and comparing the activities of the first extract and the second extract;

wherein an increase in the activity of the second extract as compared to the first extract is indicative of a drug that increases expression of a gene for apolipoprotein AI (apo AI).

15. The method of claim 14, wherein said DNA construct includes at least two copies of said DRE or its complement.

16. The method of claim 15, wherein the two copies of the DRE or its complement are arranged as an inverted repeat relative to each other.

17. The method of claim 14 or 16, wherein said construct is contained in a vector.

18. The method of claim 17, wherein said vector containing said construct is plasmid pGL2 (apoAI-DRE) TK/luc (SEQ ID No: 3).

19. The method of claim 17, wherein said vector containing said construct is plasmid pGL2 (4×apoAI-DRE) TK/luc (SEQ ID No: 4).

20. The method of claim 17, wherein said vector containing said DNA construct further includes a functional selectable marker gene, and wherein the step of maintaining the introduced DNA construct stably in the cells includes growing the cells under conditions where the marker gene is expressed.

* * * * *

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
      (A) LENGTH: 6092 base pairs
      (B) TYPE: nucleic acid
      (C) STRANDEDNESS: double
      (D) TOPOLOGY: circular (ii) MOLECULE TYPE: other nucleic acid
      (A) DESCRIPTION: /desc = "DNA (plasmid) pGL2(apo AI-491)luc"

(xi) SEQUENCE DESCRIPTION: SEQ ID NO: 1:

```
CCCGGGAGGT ACCGAGCTCT TACGCGTGCT AGCTCGGAGG CCTGAGGACC TGCTGGGGAC      60

TAAAGAAGAG CACTGGTGGG AGGACAGGGC GGGGGAAGGG GGAGGGGAGT GAAGTAGTCT     120

CCCTGGAATG CTGGTGGTGG GGGAGGCAGT CTCCTTGGTG GAGGAGTCCC AGCGTCCCTC     180

CCCTCCCCTC CTCTGCCAAC ACAATGGACA ATGGCAACTG CCCACACACT CCCATGGAGG     240

GGAAGGGGAT GAGTGCAGGG AACCCCGACC CCACCCGGGA GACCTGCAAG CCTGCAGACA     300

CTCCCCTCCC GCCCCACTG  AACCCTTGAC CCCTGCCCTG CAGCCCCGC  AGCTTGCTGT     360

TTGCCCACTC TATTTGCCCA GCCCCAGGGA CAGAGCTGAT CCTTGAACTC TTAAGTTCCA     420

CATTGCCAGG ACCAGTGAGC AGCAACAGGG CCGGGGCTGG CTTATCAGCC TCCCAGCCCA     480

GACCCTGGCT GCAGACATAA ATAGGCCCTG CAAGAGCTGG CTGCTTAGTC GAGATCTAAG     540

TAAGCTTGGC ATTCCGGTAC TGTTGGTAAA ATGGAAGACG CCAAAAACAT AAAGAAAGGC     600
```

```
CCGGCGCCAT TCTATCCTCT AGAGGATGGA ACCGCTGGAG AGCAACTGCA TAAGGCTATG      660

AAGAGATACG CCCTGGTTCC TGGAACAATT GCTTTTACAG ATGCACATAT CGAGGTGAAC      720

ATCACGTACG CGGAATACTT CGAAATGTCC GTTCGGTTGG CAGAAGCTAT GAAACGATAT      780

GGGCTGAATA CAAATCACAG AATCGTCGTA TGCAGTGAAA ACTCTCTTCA ATTCTTTATG      840

CCGGTGTTGG GCGCGTTATT TATCGGAGTT GCAGTTGCGC CCGCGAACGA CATTTATAAT      900

GAACGTGAAT TGCTCAACAG TATGAACATT TCGCAGCCTA CCGTAGTGTT TGTTTCCAAA      960

AAGGGGTTGC AAAAAATTTT GAACGTGCAA AAAAATTAC CAATAATCCA GAAAATTATT     1020

ATCATGGATT CTAAAACGGA TTACCAGGGA TTTCAGTCGA TGTACACGTT CGTCACATCT     1080

CATCTACCTC CCGGTTTTAA TGAATACGAT TTTGTACCAG AGTCCTTTGA TCGTGACAAA     1140

ACAATTGCAC TGATAATGAA TTCCTCTGGA TCTACTGGGT TACCTAAGGG TGTGGCCCTT     1200

CCGCATAGAA CTGCCTGCGT CAGATTCTCG CATGCCAGAG ATCCTATTTT TGGCAATCAA     1260

ATCATTCCGG ATACTGCGAT TTTAAGTGTT GTTCCATTCC ATCACGGTTT TGGAATGTTT     1320

ACTACACTCG GATATTTGAT ATGTGGATTT CGAGTCGTCT TAATGTATAG ATTTGAAGAA     1380

GAGCTGTTTT TACGATCCCT TCAGGATTAC AAAAATTCAAA GTGCGTTGCT AGTACCAACC     1440

CTATTTTCAT TCTTCGCCAA AAGCACTCTG ATTGACAAAT ACGATTTATC TAATTTACAC     1500

GAAATTGCTT CTGGGGCGC ACCTCTTTCG AAAGAAGTCG GGGAAGCGGT TGCAAAACGC      1560

TTCCATCTTC CAGGGATACG ACAAGGATAT GGGCTCACTG AGACTACATC AGCTATTCTG     1620

ATTACACCCG AGGGGATGA TAAACCGGGC GCGGTCGGTA AAGTTGTTCC ATTTTTTGAA      1680

GCGAAGGTTG TGGATCTGGA TACCGGGAAA ACGCTGGGCG TTAATCAGAG AGGCGAATTA     1740

TGTGTCAGAG GACCTATGAT TATGTCCGGT TATGTAAACA ATCCGGAAGC GACCAACGCC     1800

TTGATTGACA AGGATGGATG GCTACATTCT GGAGACATAG CTTACTGGGA CGAAGACGAA     1860

CACTTCTTCA TAGTTGACCG CTTGAAGTCT TTAATTAAAT ACAAAGGATA TCAGGTGGCC     1920

CCCGCTGAAT TGGAATCGAT ATTGTTACAA CACCCCAACA TCTTCGACGC GGGCGTGGCA     1980

GGTCTTCCCG ACGATGACGC CGGTGAACTT CCCGCCGCCG TTGTTGTTTT GGAGCACGGA     2040

AAGACGATGA CGGAAAAAGA GATCGTGGAT TACGTCGCCA GTCAAGTAAC AACCGCGAAA     2100

AAGTTGCGCG GAGGAGTTGT GTTTGTGGAC GAAGTACCGA AAGGTCTTAC CGGAAAACTC     2160

GACGCAAGAA AAATCAGAGA GATCCTCATA AAGGCCAAGA AGGGCGGAAA GTCCAAATTG     2220

TAAAATGTAA CTGTATTCAG CGATGACGAA ATTCTTAGCT ATTGTAATAC TGCGATGAGT     2280

GGCAGGGCGG GGCGTAATTT TTTTAAGGCA GTTATTGGTG CCCTTAAACG CCTGGTGCTA     2340

CGCCTGAATA AGTGATAATA AGCGGATGAA TGGCAGAAAT TCGCCGGATC TTTGTGAAGG     2400

AACCTTACTT CTGTGGTGTG ACATAATTGG ACAAACTACC TACAGAGATT TAAAGCTCTA     2460

AGGTAAATAT AAAATTTTTA AGTGTATAAT GTGTTAAACT ACTGATTCTA ATTGTTTGTG     2520

TATTTTAGAT TCCAACCTAT GGAACTGATG AATGGGAGCA GTGGTGGAAT GCCTTTAATG     2580

AGGAAAACCT GTTTTGCTCA GAAGAAATGC CATCTAGTGA TGATGAGGCT ACTGCTGACT     2640

CTCAACATTC TACTCCTCCA AAAAAGAAGA GAAAGGTAGA AGACCCCAAG GACTTTCCTT     2700

CAGAATTGCT AAGTTTTTTG AGTCATGCTG TGTTTAGTAA TAGAACTCTT GCTTGCTTTG     2760

CTATTTACAC CACAAAGGAA AAAGCTGCAC TGCTATACAA GAAAATTATG GAAAAATATT     2820

CTGTAACCTT TATAAGTAGG CATAACAGTT ATAATCATAA CATACTGTTT TTCTTACTC     2880

CACACAGGCA TAGAGTGTCT GCTATTAATA ACTATGCTCA AAAATTGTGT ACCTTTAGCT     2940

TTTTAATTTG TAAAGGGGTT AATAAGGAAT ATTTGATGTA TAGTGCCTTG ACTAGAGATC     3000
```

```
ATAATCAGCC ATACCACATT TGTAGAGGTT TTACTTGCTT TAAAAAACCT CCCACACCTC    3060

CCCCTGAACC TGAAACATAA AATGAATGCA ATTGTTGTTG TTAACTTGTT TATTGCAGCT    3120

TATAATGGTT ACAAATAAAG CAATAGCATC ACAAATTTCA CAAATAAAGC ATTTTTTTCA    3180

CTGCATTCTA GTTGTGGTTT GTCCAAACTC ATCAATGTAT CTTATCATGT CTGGATCCGT    3240

CGACCGATGC CCTTGAGAGC CTTCAACCCA GTCAGCTCCT TCCGGTGGGC GCGGGGCATG    3300

ACTATCGTCG CCGCACTTAT GACTGTCTTC TTTATCATGC AACTCGTAGG ACAGGTGCCG    3360

GCAGCGCTCT TCCGCTTCCT CGCTCACTGA CTCGCTGCGC TCGGTCGTTC GGCTGCGGCG    3420

AGCGGTATCA GCTCACTCAA AGGCGGTAAT ACGGTTATCC ACAGAATCAG GGGATAACGC    3480

AGGAAAGAAC ATGTGAGCAA AAGGCCAGCA AAAGGCCAGG AACCGTAAAA AGGCCGCGTT    3540

GCTGGCGTTT TTCCATAGGC TCCGCCCCCC TGACGAGCAT CACAAAAATC GACGCTCAAG    3600

TCAGAGGTGG CGAAACCCGA CAGGACTATA AAGATACCAG GCGTTTCCCC CTGGAAGCTC    3660

CCTCGTGCGC TCTCCTGTTC CGACCCTGCC GCTTACCGGA TACCTGTCCG CCTTTCTCCC    3720

TTCGGGAAGC GTGGCGCTTT CTCAATGCTC ACGCTGTAGG TATCTCAGTT CGGTGTAGGT    3780

CGTTCGCTCC AAGCTGGGCT GTGTGCACGA ACCCCCCGTT CAGCCCGACC GCTGCGCCTT    3840

ATCCGGTAAC TATCGTCTTG AGTCCAACCC GGTAAGACAC GACTTATCGC CACTGGCAGC    3900

AGCCACTGGT AACAGGATTA GCAGAGCGAG GTATGTAGGC GGTGCTACAG AGTTCTTGAA    3960

GTGGTGGCCT AACTACGGCT ACACTAGAAG GACAGTATTT GGTATCTGCG CTCTGCTGAA    4020

GCCAGTTACC TTCGGAAAAA GAGTTGGTAG CTCTTGATCC GGCAAACAAA CCACCGCTGG    4080

TAGCGGTGGT TTTTTTGTTT GCAAGCAGCA GATTACGCGC AGAAAAAAAG GATCTCAAGA    4140

AGATCCTTTG ATCTTTTCTA CGGGGTCTGA CGCTCAGTGG AACGAAAACT CACGTTAAGG    4200

GATTTTGGTC ATGAGATTAT CAAAAAGGAT CTTCACCTAG ATCCTTTTAA ATTAAAAATG    4260

AAGTTTTAAA TCAATCTAAA GTATATATGA GTAAACTTGG TCTGACAGTT ACCAATGCTT    4320

AATCAGTGAG GCACCTATCT CAGCGATCTG TCTATTTCGT TCATCCATAG TTGCCTGACT    4380

CCCCGTCGTG TAGATAACTA CGATACGGGA GGGCTTACCA TCTGGCCCCA GTGCTGCAAT    4440

GATACCGCGA GACCCACGCT CACCGGCTCC AGATTTATCA GCAATAAACC AGCCAGCCGG    4500

AAGGGCCGAG CGCAGAAGTG GTCCTGCAAC TTTATCCGCC TCCATCCAGT CTATTAATTG    4560

TTGCCGGGAA GCTAGAGTAA GTAGTTCGCC AGTTAATAGT TTGCGCAACG TTGTTGCCAT    4620

TGCTACAGGC ATCGTGGTGT CACGCTCGTC GTTTGGTATG GCTTCATTCA GCTCCGGTTC    4680

CCAACGATCA AGGCGAGTTA CATGATCCCC CATGTTGTGC AAAAAAGCGG TTAGCTCCTT    4740

CGGTCCTCCG ATCGTTGTCA GAAGTAAGTT GGCCGCAGTG TTATCACTCA TGGTTATGGC    4800

AGCACTGCAT AATTCTCTTA CTGTCATGCC ATCCGTAAGA TGCTTTTCTG TGACTGGTGA    4860

GTACTCAACC AAGTCATTCT GAGAATAGTG TATGCGGCGA CCGAGTTGCT CTTGCCCGGC    4920

GTCAATACGG GATAATACCG CGCCACATAG CAGAACTTTA AAAGTGCTCA TCATTGGAAA    4980

ACGTTCTTCG GGGCGAAAAC TCTCAAGGAT CTTACCGCTG TTGAGATCCA GTTCGATGTA    5040

ACCCACTCGT GCACCCAACT GATCTTCAGC ATCTTTTACT TTCACCAGCG TTTCTGGGTG    5100

AGCAAAAACA GGAAGGCAAA ATGCCGCAAA AAAGGGAATA AGGGCGACAC GGAAATGTTG    5160

AATACTCATA CTCTTCCTTT TTCAATATTA TTGAAGCATT TATCAGGGTT ATTGTCTCAT    5220

GAGCGGATAC ATATTTGAAT GTATTTAGAA AAATAAACAA ATAGGGGTTC CGCGCACATT    5280

TCCCCGAAAA GTGCCACCTG ACGCGCCCTG TAGCGGCGCA TTAAGCGCGG CGGGTGTGGT    5340

GGTTACGCGC AGCGTGACCG CTACACTTGC CAGCGCCCTA GCGCCCGCTC CTTTCGCTTT    5400
```

```
CTTCCCTTCC TTTCTCGCCA CGTTCGCCGG CTTTCCCCGT CAAGCTCTAA ATCGGGGCT      5460

CCCTTTAGGG TTCCGATTTA GTGCTTTACG GCACCTCGAC CCCAAAAAAC TTGATTAGGG     5520

TGATGGTTCA CGTAGTGGGC CATCGCCCTG ATAGACGGTT TTTCGCCCTT TGACGTTGGA     5580

GTCCACGTTC TTTAATAGTG GACTCTTGTT CCAAACTGGA ACAACACTCA ACCCTATCTC     5640

GGTCTATTCT TTTGATTTAT AAGGGATTTT GCCGATTTCG GCCTATTGGT TAAAAAATGA     5700

GCTGATTTAA CAAAAATTTA ACGCGAATTT TAACAAAATA TTAACGTTTA CAATTTCCCA     5760

TTCGCCATTC AGGCTGCGCA ACTGTTGGGA AGGGCGATCG GTGCGGGCCT CTTCGCTATT     5820

ACGCCAGCCC AAGCTACCAT GATAAGTAAG TAATATTAAG GTACGTGGAG GTTTTACTTG     5880

CTTTAAAAAA CCTCCCACAC CTCCCCCTGA ACCTGAAACA TAAAATGAAT GCAATTGTTG     5940

TTGTTAACTT GTTTATTGCA GCTTATAATG GTTACAAATA AAGCAATAGC ATCACAAATT     6000

TCACAAATAA AGCATTTTTT TCACTGCATT CTAGTTGTGG TTTGTCCAAA CTCATCAATG     6060

TATCTTATGG TACTGTAACT GAGCTAACAT AA                                  6092
```

(2) INFORMATION FOR SEQ ID NO: 2:

(i) SEQUENCE CHARACTERISTICS:
        (A) LENGTH: 5819 base pairs
        (B) TYPE: nucleic acid
        (C) STRANDEDNESS: double
        (D) TOPOLOGY: circular (ii) MOLECULE TYPE: other nucleic acid
        (A) DESCRIPTION: /desc = "DNA (plasmid) pGL2(apo
           AI-250)luc"

(xi) SEQUENCE DESCRIPTION: SEQ ID NO: 2:

```
CCCGGGAGAC CTGCAAGCCT GCAGACACTC CCCTCCCGCC CCCACTGAAC CCTTGACCCC       60

TGCCCTGCAG CCCCCGCAGC TTGCTGTTTG CCCACTCTAT TTGCCCAGCC CCAGGGACAG      120

AGCTGATCCT TGAACTCTTA AGTTCCACAT TGCCAGGACC AGTGAGCAGC AACAGGGCCG      180

GGGCTGGCTT ATCAGCCTCC CAGCCCAGAC CCTGGCTGCA GACATAAATA GGCCCTGCAA      240

GAGCTGGCTG CTTAGTCGAG ATCTAAGTAA GCTTGGCATT CCGGTACTGT TGGTAAAATG      300

GAAGACGCCA AAAACATAAA GAAAGGCCCG GCGCCATTCT ATCCTCTAGA GGATGGAACC      360

GCTGGAGAGC AACTGCATAA GGCTATGAAG AGATACGCCC TGGTTCCTGG AACAATTGCT      420

TTTACAGATG CACATATCGA GGTGAACATC ACGTACGCGG AATACTTCGA AATGTCCGTT      480

CGGTTGGCAG AAGCTATGAA ACGATATGGG CTGAATACAA ATCACAGAAT CGTCGTATGC      540

AGTGAAAACT CTCTTCAATT CTTTATGCCG GTGTTGGGCG CGTTATTTAT CGGAGTTGCA      600

GTTGCGCCCG CGAACGACAT TTATAATGAA CGTGAATTGC TCAACAGTAT GAACATTTCG      660

CAGCCTACCG TAGTGTTTGT TTCCAAAAAG GGGTTGCAAA AAATTTTGAA CGTGCAAAAA      720

AAATTACCAA TAATCCAGAA AATTATTATC ATGGATTCTA AAACGGATTA CCAGGGATTT      780

CAGTCGATGT ACACGTTCGT CACATCTCAT CTACCTCCCG GTTTTAATGA ATACGATTTT      840

GTACCAGAGT CCTTTGATCG TGACAAAACA ATTGCACTGA TAATGAATTC CTCTGGATCT      900

ACTGGGTTAC CTAAGGGTGT GGCCCTTCCG CATAGAACTG CCTGCGTCAG ATTCTCGCAT      960

GCCAGAGATC CTATTTTTGG CAATCAAATC ATTCCGGATA CTGCGATTTT AAGTGTTGTT     1020

CCATTCCATC ACGGTTTTGG AATGTTTACT ACACTCGGAT ATTTGATATG TGGATTTCGA     1080

GTCGTCTTAA TGTATAGATT TGAAGAAGAG CTGTTTTTAC GATCCCTTCA GGATTACAAA     1140

ATTCAAAGTG CGTTGCTAGT ACCAACCCTA TTTTCATTCT TCGCCAAAAG CACTCTGATT     1200

GACAAATACG ATTTATCTAA TTTACACGAA ATTGCTTCTG GGGGCGCACC TCTTTCGAAA     1260
```

```
GAAGTCGGGG AAGCGGTTGC AAAACGCTTC CATCTTCCAG GGATACGACA AGGATATGGG   1320

CTCACTGAGA CTACATCAGC TATTCTGATT ACACCCGAGG GGGATGATAA ACCGGGCGCG   1380

GTCGGTAAAG TTGTTCCATT TTTTGAAGCG AAGGTTGTGG ATCTGGATAC CGGGAAAACG   1440

CTGGGCGTTA ATCAGAGAGG CGAATTATGT GTCAGAGGAC CTATGATTAT GTCCGGTTAT   1500

GTAAACAATC CGGAAGCGAC CAACGCCTTG ATTGACAAGG ATGGATGGCT ACATTCTGGA   1560

GACATAGCTT ACTGGGACGA AGACGAACAC TTCTTCATAG TTGACCGCTT GAAGTCTTTA   1620

ATTAAATACA AAGGATATCA GGTGGCCCCC GCTGAATTGG AATCGATATT GTTACAACAC   1680

CCCAACATCT TCGACGCGGG CGTGGCAGGT CTTCCCGACG ATGACGCCGG TGAACTTCCC   1740

GCCGCCGTTG TTGTTTTGGA GCACGGAAAG ACGATGACGG AAAAAGAGAT CGTGGATTAC   1800

GTCGCCAGTC AAGTAACAAC CGCGAAAAAG TTGCGCGGAG GAGTTGTGTT TGTGGACGAA   1860

GTACCGAAAG GTCTTACCGG AAAACTCGAC GCAAGAAAAA TCAGAGAGAT CCTCATAAAG   1920

GCCAAGAAGG GCGGAAAGTC CAAATTGTAA AATGTAACTG TATTCAGCGA TGACGAAATT   1980

CTTAGCTATT GTAATACTGC GATGAGTGGC AGGGCGGGC GTAATTTTTT TAAGGCAGTT   2040

ATTGGTGCCC TTAAACGCCT GGTGCTACGC CTGAATAAGT GATAATAAGC GGATGAATGG   2100

CAGAAATTCG CCGGATCTTT GTGAAGGAAC CTTACTTCTG TGGTGTGACA TAATTGGACA   2160

AACTACCTAC AGAGATTTAA AGCTCTAAGG TAAATATAAA ATTTTTAAGT GTATAATGTG   2220

TTAAACTACT GATTCTAATT GTTTGTGTAT TTTAGATTCC AACCTATGGA ACTGATGAAT   2280

GGGAGCAGTG GTGGAATGCC TTTAATGAGG AAAACCTGTT TTGCTCAGAA GAAATGCCAT   2340

CTAGTGATGA TGAGGCTACT GCTGACTCTC AACATTCTAC TCCTCCAAAA AAGAAGAGAA   2400

AGGTAGAAGA CCCCAAGGAC TTTCCTTCAG AATTGCTAAG TTTTTTGAGT CATGCTGTGT   2460

TTAGTAATAG AACTCTTGCT TGCTTTGCTA TTTACACCAC AAAGGAAAAA GCTGCACTGC   2520

TATACAAGAA AATTATGGAA AAATATTCTG TAACCTTTAT AAGTAGGCAT AACAGTTATA   2580

ATCATAACAT ACTGTTTTTT CTTACTCCAC ACAGGCATAG AGTGTCTGCT ATTAATAACT   2640

ATGCTCAAAA ATTGTGTACC TTTAGCTTTT TAATTTGTAA AGGGGTTAAT AAGGAATATT   2700

TGATGTATAG TGCCTTGACT AGAGATCATA ATCAGCCATA CCACATTTGT AGAGGTTTTA   2760

CTTGCTTTAA AAAACCTCCC ACACCTCCCC CTGAACCTGA AACATAAAAT GAATGCAATT   2820

GTTGTTGTTA ACTTGTTTAT TGCAGCTTAT AATGGTTACA AATAAAGCAA TAGCATCACA   2880

AATTTCACAA ATAAAGCATT TTTTTCACTG CATTCTAGTT GTGGTTTGTC CAAACTCATC   2940

AATGTATCTT ATCATGTCTG GATCCGTCGA CCGATGCCCT TGAGAGCCTT CAACCCAGTC   3000

AGCTCCTTCC GGTGGGCGCG GGGCATGACT ATCGTCGCCG CACTTATGAC TGTCTTCTTT   3060

ATCATGCAAC TCGTAGGACA GGTGCCGGCA GCGCTCTTCC GCTTCCTCGC TCACTGACTC   3120

GCTGCGCTCG GTCGTTCGGC TGCGGCGAGC GGTATCAGCT CACTCAAAGG CGGTAATACG   3180

GTTATCCACA GAATCAGGGG ATAACGCAGG AAAGAACATG TGAGCAAAAG GCCAGCAAAA   3240

GGCCAGGAAC CGTAAAAAGG CCGCGTTGCT GGCGTTTTTC CATAGGCTCC GCCCCCCTGA   3300

CGAGCATCAC AAAAATCGAC GCTCAAGTCA GAGGTGGCGA AACCCGACAG GACTATAAAG   3360

ATACCAGGCG TTTCCCCCTG GAAGCTCCCT CGTGCGCTCT CCTGTTCCGA CCCTGCCGCT   3420

TACCGGATAC CTGTCCGCCT TTCTCCCTTC GGGAAGCGTG GCGCTTTCTC AATGCTCACG   3480

CTGTAGGTAT CTCAGTTCGG TGTAGGTCGT TCGCTCCAAG CTGGGCTGTG TGCACGAACC   3540

CCCCGTTCAG CCCGACCGCT GCGCCTTATC CGGTAACTAT CGTCTTGAGT CCAACCCGGT   3600

AAGACACGAC TTATCGCCAC TGGCAGCAGC CACTGGTAAC AGGATTAGCA GAGCGAGGTA   3660
```

```
TGTAGGCGGT GCTACAGAGT TCTTGAAGTG GTGGCCTAAC TACGGCTACA CTAGAAGGAC   3720

AGTATTTGGT ATCTGCGCTC TGCTGAAGCC AGTTACCTTC GGAAAAAGAG TTGGTAGCTC   3780

TTGATCCGGC AAACAAACCA CCGCTGGTAG CGGTGGTTTT TTTGTTTGCA AGCAGCAGAT   3840

TACGCGCAGA AAAAAAGGAT CTCAAGAAGA TCCTTTGATC TTTTCTACGG GGTCTGACGC   3900

TCAGTGGAAC GAAAACTCAC GTTAAGGGAT TTTGGTCATG AGATTATCAA AAAGGATCTT   3960

CACCTAGATC CTTTTAAATT AAAAATGAAG TTTTAAATCA ATCTAAAGTA TATATGAGTA   4020

AACTTGGTCT GACAGTTACC AATGCTTAAT CAGTGAGGCA CCTATCTCAG CGATCTGTCT   4080

ATTTCGTTCA TCCATAGTTG CCTGACTCCC CGTCGTGTAG ATAACTACGA TACGGGAGGG   4140

CTTACCATCT GGCCCCAGTG CTGCAATGAT ACCGCGAGAC CCACGCTCAC CGGCTCCAGA   4200

TTTATCAGCA ATAAACCAGC CAGCCGGAAG GGCCGAGCGC AGAAGTGGTC CTGCAACTTT   4260

ATCCGCCTCC ATCCAGTCTA TTAATTGTTG CCGGGAAGCT AGAGTAAGTA GTTCGCCAGT   4320

TAATAGTTTG CGCAACGTTG TTGCCATTGC TACAGGCATC GTGGTGTCAC GCTCGTCGTT   4380

TGGTATGGCT TCATTCAGCT CCGGTTCCCA ACGATCAAGG CGAGTTACAT GATCCCCCAT   4440

GTTGTGCAAA AAAGCGGTTA GCTCCTTCGG TCCTCCGATC GTTGTCAGAA GTAAGTTGGC   4500

CGCAGTGTTA TCACTCATGG TTATGGCAGC ACTGCATAAT TCTCTTACTG TCATGCCATC   4560

CGTAAGATGC TTTTCTGTGA CTGGTGAGTA CTCAACCAAG TCATTCTGAG AATAGTGTAT   4620

GCGGCGACCG AGTTGCTCTT GCCCGGCGTC AATACGGGAT AATACCGCGC CACATAGCAG   4680

AACTTTAAAA GTGCTCATCA TTGGAAAACG TTCTTCGGGG CGAAAACTCT CAAGGATCTT   4740

ACCGCTGTTG AGATCCAGTT CGATGTAACC CACTCGTGCA CCCAACTGAT CTTCAGCATC   4800

TTTTACTTTC ACCAGCGTTT CTGGGTGAGC AAAAACAGGA AGGCAAAATG CCGCAAAAAA   4860

GGGAATAAGG GCGACACGGA AATGTTGAAT ACTCATACTC TTCCTTTTTC AATATTATTG   4920

AAGCATTTAT CAGGGTTATT GTCTCATGAG CGGATACATA TTTGAATGTA TTTAGAAAAA   4980

TAAACAAATA GGGGTTCCGC GCACATTTCC CCGAAAAGTG CCACCTGACG CGCCCTGTAG   5040

CGGCGCATTA AGCGCGGCGG GTGTGGTGGT TACGCGCAGC GTGACCGCTA CACTTGCCAG   5100

CGCCCTAGCG CCCGCTCCTT TCGCTTTCTT CCCTTCCTTT CTCGCCACGT TCGCCGGCTT   5160

TCCCCGTCAA GCTCTAAATC GGGGGCTCCC TTTAGGGTTC CGATTTAGTG CTTTACGGCA   5220

CCTCGACCCC AAAAAACTTG ATTAGGGTGA TGGTTCACGT AGTGGGCCAT CGCCCTGATA   5280

GACGGTTTTT CGCCCTTTGA CGTTGGAGTC CACGTTCTTT AATAGTGGAC TCTTGTTCCA   5340

AACTGGAACA ACACTCAACC CTATCTCGGT CTATTCTTTT GATTTATAAG GGATTTTGCC   5400

GATTTCGGCC TATTGGTTAA AAAATGAGCT GATTTAACAA AAATTTAACG CGAATTTTAA   5460

CAAAATATTA ACGTTTACAA TTTCCCATTC GCCATTCAGG CTGCGCAACT GTTGGGAAGG   5520

GCGATCGGTG CGGGCCTCTT CGCTATTACG CCAGCCCAAG CTACCATGAT AAGTAAGTAA   5580

TATTAAGGTA CGTGGAGGTT TTACTTGCTT TAAAAAACCT CCCACACCTC CCCCTGAACC   5640

TGAAACATAA AATGAATGCA ATTGTTGTTG TTAACTTGTT TATTGCAGCT TATAATGGTT   5700

ACAAATAAAG CAATAGCATC ACAAATTTCA CAAATAAAGC ATTTTTTTCA CTGCATTCTA   5760

GTTGTGGTTT GTCCAAACTC ATCAATGTAT CTTATGGTAC TGTAACTGAG CTAACATAA    5819
```

(2) INFORMATION FOR SEQ ID NO: 3:

(i) SEQUENCE CHARACTERISTICS:
        (A) LENGTH: 5818 base pairs
        (B) TYPE: nucleic acid
        (C) STRANDEDNESS: double (D) TOPOLOGY: circular (ii) MOLECULE TYPE: other nucleic acid
    (A) DESCRIPTION: /desc = "DNA (plasmid) pGL2(apo
        AI-DRE)TK/luc"

(xi) SEQUENCE DESCRIPTION: SEQ ID NO: 3:

```
CCCGGGAGGT ACCGAGCTCT TACGCGTGCT AGCTCGTGGT GGCCGGGGCT GGCTTATCAG      60

CCTCCCAGCC CAGACCTGGT TCGAGATCCG GCCCCGCCCA GCGTCTTGTC TTGTCATTGG     120

CGTTGGCGAA TTCGAACACG CAGAGTCAGT CGGGGCGGCG CGGTCCGAGG TCCACTTCGC     180

ATATTAAGGT GACGCGTGTG GCCTCGAACA CCGAGCGACC CTGCAGCGAC CGCTTAACAG     240

CGTCAACAGC GTGCCGCAGA TCTAAGTAAG CTTGGCATTC CGGTACTGTT GGTAAAATGG     300

AAGACGCCAA AAACATAAAG AAAGGCCCGG CGCCATTCTA TCCTCTAGAG GATGGAACCG     360

CTGGAGAGCA ACTGCATAAG GCTATGAAGA GATACGCCCT GGTTCCTGGA ACAATTGCTT     420

TTACAGATGC ACATATCGAG GTGAACATCA CGTACGCGGA ATACTTCGAA ATGTCCGTTC     480

GGTTGGCAGA AGCTATGAAA CGATATGGGC TGAATACAAA TCACAGAATC GTCGTATGCA     540

GTGAAAACTC TCTTCAATTC TTTATGCCGG TGTTGGGCGC GTTATTTATC GGAGTTGCAG     600

TTGCGCCCGC GAACGACATT TATAATGAAC GTGAATTGCT CAACAGTATG AACATTTCGC     660

AGCCTACCGT AGTGTTTGTT TCCAAAAAGG GGTTGCAAAA AATTTTGAAC GTGCAAAAAA     720

AATTACCAAT AATCCAGAAA ATTATTATCA TGGATTCTAA AACGGATTAC CAGGGATTTC     780

AGTCGATGTA CACGTTCGTC ACATCTCATC TACCTCCCGG TTTTAATGAA TACGATTTTG     840

TACCAGAGTC CTTTGATCGT GACAAAACAA TTGCACTGAT AATGAATTCC TCTGGATCTA     900

CTGGGTTACC TAAGGGTGTG GCCCTTCCGC ATAGAACTGC CTGCGTCAGA TTCTCGCATG     960

CCAGAGATCC TATTTTTGGC AATCAAATCA TTCCGGATAC TGCGATTTTA AGTGTTGTTC    1020

CATTCCATCA CGGTTTTGGA ATGTTTACTA CACTCGGATA TTTGATATGT GGATTTCGAG    1080

TCGTCTTAAT GTATAGATTT GAAGAAGAGC TGTTTTTACG ATCCCTTCAG GATTACAAAA    1140

TTCAAAGTGC GTTGCTAGTA CCAACCCTAT TTTCATTCTT CGCCAAAAGC ACTCTGATTG    1200

ACAAATACGA TTTATCTAAT TTACACGAAA TTGCTTCTGG GGGCGCACCT CTTTCGAAAG    1260

AAGTCGGGGA AGCGGTTGCA AAACGCTTCC ATCTTCCAGG GATACGACAA GGATATGGGC    1320

TCACTGAGAC TACATCAGCT ATTCTGATTA CACCCGAGGG GGATGATAAA CCGGGCGCGG    1380

TCGGTAAAGT TGTTCCATTT TTTGAAGCGA AGGTTGTGGA TCTGGATACC GGGAAAACGC    1440

TGGGCGTTAA TCAGAGAGGC GAATTATGTG TCAGAGGACC TATGATTATG TCCGGTTATG    1500

TAAACAATCC GGAAGCGACC AACGCCTTGA TTGACAAGGA TGGATGGCTA CATTCTGGAG    1560

ACATAGCTTA CTGGGACGAA GACGAACACT TCTTCATAGT TGACCGCTTG AAGTCTTTAA    1620

TTAAATACAA AGGATATCAG GTGGCCCCCG CTGAATTGGA ATCGATATTG TTACAACACC    1680

CCAACATCTT CGACGCGGGC GTGGCAGGTC TTCCCGACGA TGACGCCGGT GAACTTCCCG    1740

CCGCCGTTGT TGTTTTGGAG CACGGAAAGA CGATGACGGA AAAAGAGATC GTGGATTACG    1800

TCGCCAGTCA AGTAACAACC GCGAAAAAGT TGCGCGGAGG AGTTGTGTTT GTGGACGAAG    1860

TACCGAAAGG TCTTACCGGA AAACTCGACG CAAGAAAAAT CAGAGAGATC CTCATAAAGG    1920

CCAAGAAGGG CGGAAAGTCC AAATTGTAAA ATGTAACTGT ATTCAGCGAT GACGAAATTC    1980

TTAGCTATTG TAATACTGCG ATGAGTGGCA GGGCGGGGCG TAATTTTTTT AAGGCAGTTA    2040

TTGGTGCCCT TAAACGCCTG GTGCTACGCC TGAATAAGTG ATAATAAGCG GATGAATGGC    2100

AGAAATTCGC CGGATCTTTG TGAAGGAACC TTACTTCTGT GGTGTGACAT AATTGGACAA    2160
```

```
ACTACCTACA GAGATTTAAA GCTCTAAGGT AAATATAAAA TTTTTAAGTG TATAATGTGT    2220

TAAACTACTG ATTCTAATTG TTTGTGTATT TTAGATTCCA ACCTATGGAA CTGATGAATG    2280

GGAGCAGTGG TGGAATGCCT TTAATGAGGA AAACCTGTTT TGCTCAGAAG AAATGCCATC    2340

TAGTGATGAT GAGGCTACTG CTGACTCTCA ACATTCTACT CCTCCAAAAA AGAAGAGAAA    2400

GGTAGAAGAC CCCAAGGACT TTCCTTCAGA ATTGCTAAGT TTTTTGAGTC ATGCTGTGTT    2460

TAGTAATAGA ACTCTTGCTT GCTTTGCTAT TTACACCACA AAGGAAAAAG CTGCACTGCT    2520

ATACAAGAAA ATTATGGAAA AATATTCTGT AACCTTTATA AGTAGGCATA ACAGTTATAA    2580

TCATAACATA CTGTTTTTTC TTACTCCACA CAGGCATAGA GTGTCTGCTA TTAATAACTA    2640

TGCTCAAAAA TTGTGTACCT TTAGCTTTTT AATTTGTAAA GGGGTTAATA AGGAATATTT    2700

GATGTATAGT GCCTTGACTA GAGATCATAA TCAGCCATAC CACATTTGTA GAGGTTTTAC    2760

TTGCTTTAAA AAACCTCCCA CACCTCCCCC TGAACCTGAA ACATAAAATG AATGCAATTG    2820

TTGTTGTTAA CTTGTTTATT GCAGCTTATA ATGGTTACAA ATAAAGCAAT AGCATCACAA    2880

ATTTCACAAA TAAAGCATTT TTTTCACTGC ATTCTAGTTG TGGTTTGTCC AAACTCATCA    2940

ATGTATCTTA TCATGTCTGG ATCCGTCGAC CGATGCCCTT GAGAGCCTTC AACCCAGTCA    3000

GCTCCTTCCG GTGGGCGCGG GGCATGACTA TCGTCGCCGC ACTTATGACT GTCTTCTTTA    3060

TCATGCAACT CGTAGGACAG GTGCCGGCAG CGCTCTTCCG CTTCCTCGCT CACTGACTCG    3120

CTGCGCTCGG TCGTTCGGCT GCGGCGAGCG GTATCAGCTC ACTCAAAGGC GGTAATACGG    3180

TTATCCACAG AATCAGGGGA TAACGCAGGA AAGAACATGT GAGCAAAAGG CCAGCAAAAG    3240

GCCAGGAACC GTAAAAAGGC CGCGTTGCTG GCGTTTTTCC ATAGGCTCCG CCCCCCTGAC    3300

GAGCATCACA AAAATCGACG CTCAAGTCAG AGGTGGCGAA ACCCGACAGG ACTATAAAGA    3360

TACCAGGCGT TTCCCCCTGG AAGCTCCCTC GTGCGCTCTC CTGTTCCGAC CCTGCCGCTT    3420

ACCGGATACC TGTCCGCCTT TCTCCCTTCG GGAAGCGTGG CGCTTTCTCA ATGCTCACGC    3480

TGTAGGTATC TCAGTTCGGT GTAGGTCGTT CGCTCCAAGC TGGGCTGTGT GCACGAACCC    3540

CCCGTTCAGC CCGACCGCTG CGCCTTATCC GGTAACTATC GTCTTGAGTC AACCCGGTA    3600

AGACACGACT TATCGCCACT GGCAGCAGCC ACTGGTAACA GGATTAGCAG AGCGAGGTAT    3660

GTAGGCGGTG CTACAGAGTT CTTGAAGTGG TGGCCTAACT ACGGCTACAC TAGAAGGACA    3720

GTATTTGGTA TCTGCGCTCT GCTGAAGCCA GTTACCTTCG GAAAAAGAGT TGGTAGCTCT    3780

TGATCCGGCA AACAAACCAC CGCTGGTAGC GGTGGTTTTT TTGTTTGCAA GCAGCAGATT    3840

ACGCGCAGAA AAAAAGGATC TCAAGAAGAT CCTTTGATCT TTTCTACGGG GTCTGACGCT    3900

CAGTGGAACG AAAACTCACG TTAAGGGATT TTGGTCATGA GATTATCAAA AAGGATCTTC    3960

ACCTAGATCC TTTTAAATTA AAAATGAAGT TTTAAATCAA TCTAAAGTAT ATATGAGTAA    4020

ACTTGGTCTG ACAGTTACCA ATGCTTAATC AGTGAGGCAC CTATCTCAGC GATCTGTCTA    4080

TTTCGTTCAT CCATAGTTGC CTGACTCCCC GTCGTGTAGA TAACTACGAT ACGGGAGGGC    4140

TTACCATCTG GCCCCAGTGC TGCAATGATA CCGCGAGACC CACGCTCACC GGCTCCAGAT    4200

TTATCAGCAA TAAACCAGCC AGCCGGAAGG GCCGAGCGCA GAAGTGGTCC TGCAACTTTA    4260

TCCGCCTCCA TCCAGTCTAT TAATTGTTGC CGGGAAGCTA GAGTAAGTAG TTCGCCAGTT    4320

AATAGTTTGC GCAACGTTGT TGCCATTGCT ACAGGCATCG TGGTGTCACG CTCGTCGTTT    4380

GGTATGGCTT CATTCAGCTC CGGTTCCCAA CGATCAAGGC GAGTTACATG ATCCCCCATG    4440

TTGTGCAAAA AAGCGGTTAG CTCCTTCGGT CCTCCGATCG TTGTCAGAAG TAAGTTGGCC    4500

GCAGTGTTAT CACTCATGGT TATGGCAGCA CTGCATAATT CTCTTACTGT CATGCCATCC    4560
```

-continued

| | | | |
|---|---|---|---|
| GTAAGATGCT | TTTCTGTGAC TGGTGAGTAC TCAACCAAGT CATTCTGAGA ATAGTGTATG | 4620 |
| CGGCGACCGA | GTTGCTCTTG CCCGGCGTCA ATACGGGATA ATACCGCGCC ACATAGCAGA | 4680 |
| ACTTTAAAAG | TGCTCATCAT TGGAAAACGT TCTTCGGGGC GAAAACTCTC AAGGATCTTA | 4740 |
| CCGCTGTTGA | GATCCAGTTC GATGTAACCC ACTCGTGCAC CCAACTGATC TTCAGCATCT | 4800 |
| TTTACTTTCA | CCAGCGTTTC TGGGTGAGCA AAAACAGGAA GGCAAAATGC CGCAAAAAAG | 4860 |
| GGAATAAGGG | CGACACGGAA ATGTTGAATA CTCATACTCT TCCTTTTTCA ATATTATTGA | 4920 |
| AGCATTTATC | AGGGTTATTG TCTCATGAGC GGATACATAT TTGAATGTAT TTAGAAAAAT | 4980 |
| AAACAAATAG | GGGTTCCGCG CACATTTCCC CGAAAAGTGC CACCTGACGC GCCCTGTAGC | 5040 |
| GGCGCATTAA | GCGCGGCGGG TGTGGTGGTT ACGCGCAGCG TGACCGCTAC ACTTGCCAGC | 5100 |
| GCCCTAGCGC | CCGCTCCTTT CGCTTTCTTC CCTTCCTTTC TCGCCACGTT CGCCGGCTTT | 5160 |
| CCCCGTCAAG | CTCTAAATCG GGGGCTCCCT TTAGGGTTCC GATTTAGTGC TTTACGGCAC | 5220 |
| CTCGACCCCA | AAAAACTTGA TTAGGGTGAT GGTTCACGTA GTGGGCCATC GCCCTGATAG | 5280 |
| ACGGTTTTTC | GCCCTTTGAC GTTGGAGTCC ACGTTCTTTA ATAGTGGACT CTTGTTCCAA | 5340 |
| ACTGAACAA | CACTCAACCC TATCTCGGTC TATTCTTTTG ATTTATAAGG GATTTTGCCG | 5400 |
| ATTTCGGCCT | ATTGGTTAAA AAATGAGCTG ATTTAACAAA AATTTAACGC GAATTTTAAC | 5460 |
| AAAATATTAA | CGTTTACAAT TTCCCATTCG CCATTCAGGC TGCGCAACTG TTGGGAAGGG | 5520 |
| CGATCGGTGC | GGGCCTCTTC GCTATTACGC CAGCCCAAGC TACCATGATA AGTAAGTAAT | 5580 |
| ATTAAGGTAC | GTGGAGGTTT TACTTGCTTT AAAAAACCTC CCACACCTCC CCCTGAACCT | 5640 |
| GAAACATAAA | ATGAATGCAA TTGTTGTTGT TAACTTGTTT ATTGCAGCTT ATAATGGTTA | 5700 |
| CAAATAAAGC | AATAGCATCA CAAATTTCAC AAATAAAGCA TTTTTTTCAC TGCATTCTAG | 5760 |
| TTGTGGTTTG | TCCAAACTCA TCAATGTATC TTATGGTACT GTAACTGAGC TAACATAA | 5818 |

(2) INFORMATION FOR SEQ ID NO: 4:

(i) SEQUENCE CHARACTERISTICS:
        (A) LENGTH: 5938 base pairs
        (B) TYPE: nucleic acid
        (C) STRANDEDNESS: double
        (D) TOPOLOGY: circular (ii) MOLECULE TYPE: other nucleic acid
        (A) DESCRIPTION: /desc = "DNA (plasmid) pGL2(4x apo
           AI-DRE)TK/luc"

(xi) SEQUENCE DESCRIPTION: SEQ ID NO: 4:

| | | |
|---|---|---|
| CCCGGGAGGT ACCGAGCTCT TACGCGTGCT AGCTCGTGGT GGCCGGGGCT GGCTTATCAG | 60 |
| CCTCCCAGCC CAGACCTGGT GGCCGGGGCT GGCTTATCAG CCTCCCAGCC CAGACCTGGT | 120 |
| GGCCGGGGCT GGCTTATCAG CCTCCCAGCC CAGACCTGGT GGCCGGGGCT GGCTTATCAG | 180 |
| CCTCCCAGCC CAGACCTGGT TCGAGATCCG GCCCCGCCCA GCGTCTTGTC TTGTCATTGG | 240 |
| CGTTGGCGAA TTCGAACACG CAGAGTCAGT CGGGGCGGCG CGGTCCGAGG TCCACTTCGC | 300 |
| ATATTAAGGT GACGCGTGTG GCCTCGAACA CCGAGCGACC CTGCAGCGAC CGCTTAACAG | 360 |
| CGTCAACAGC GTGCCGCAGA TCTAAGTAAG CTTGGCATTC CGGTACTGTT GGTAAAATGG | 420 |
| AAGACGCCAA AACATAAAG AAAGGCCCGG CGCCATTCTA TCCTCTAGAG GATGAACCG | 480 |
| CTGGAGAGCA ACTGCATAAG GCTATGAAGA GATACGCCCT GGTTCCTGGA ACAATTGCTT | 540 |
| TTACAGATGC ACATATCGAG GTGAACATCA CGTACGCGGA ATACTTCGAA ATGTCCGTTC | 600 |
| GGTTGGCAGA AGCTATGAAA CGATATGGGC TGAATACAAA TCACAGAATC GTCGTATGCA | 660 |
| GTGAAAACTC TCTTCAATTC TTTATGCCGG TGTTGGGCGC GTTATTTATC GGAGTTGCAG | 720 |

| | |
|---|---|
| TTGCGCCCGC GAACGACATT TATAATGAAC GTGAATTGCT CAACAGTATG AACATTTCGC | 780 |
| AGCCTACCGT AGTGTTTGTT TCCAAAAAGG GGTTGCAAAA AATTTTGAAC GTGCAAAAAA | 840 |
| AATTACCAAT AATCCAGAAA ATTATTATCA TGGATTCTAA AACGGATTAC CAGGGATTTC | 900 |
| AGTCGATGTA CACGTTCGTC ACATCTCATC TACCTCCCGG TTTTAATGAA TACGATTTTG | 960 |
| TACCAGAGTC CTTTGATCGT GACAAAACAA TTGCACTGAT AATGAATTCC TCTGGATCTA | 1020 |
| CTGGGTTACC TAAGGGTGTG GCCCTTCCGC ATAGAACTGC CTGCGTCAGA TTCTCGCATG | 1080 |
| CCAGAGATCC TATTTTTGGC AATCAAATCA TTCCGGATAC TGCGATTTTA AGTGTTGTTC | 1140 |
| CATTCCATCA CGGTTTTGGA ATGTTTACTA CACTCGGATA TTTGATATGT GGATTTCGAG | 1200 |
| TCGTCTTAAT GTATAGATTT GAAGAAGAGC TGTTTTTACG ATCCCTTCAG GATTACAAAA | 1260 |
| TTCAAAGTGC GTTGCTAGTA CCAACCCTAT TTTCATTCTT CGCCAAAAGC ACTCTGATTG | 1320 |
| ACAAATACGA TTTATCTAAT TTACACGAAA TTGCTTCTGG GGGCGCACCT CTTTCGAAAG | 1380 |
| AAGTCGGGGA AGCGGTTGCA AAACGCTTCC ATCTTCCAGG GATACGACAA GGATATGGGC | 1440 |
| TCACTGAGAC TACATCAGCT ATTCTGATTA CACCCGAGGG GGATGATAAA CCGGGCGCGG | 1500 |
| TCGGTAAAGT TGTTCCATTT TTTGAAGCGA AGGTTGTGGA TCTGGATACC GGGAAAACGC | 1560 |
| TGGGCGTTAA TCAGAGAGGC GAATTATGTG TCAGAGGACC TATGATTATG TCCGGTTATG | 1620 |
| TAAACAATCC GGAAGCGACC AACGCCTTGA TTGACAAGGA TGGATGGCTA CATTCTGGAG | 1680 |
| ACATAGCTTA CTGGGACGAA GACGAACACT TCTTCATAGT TGACCGCTTG AAGTCTTTAA | 1740 |
| TTAAATACAA AGGATATCAG GTGGCCCCCG CTGAATTGGA ATCGATATTG TTACAACACC | 1800 |
| CCAACATCTT CGACGCGGGC GTGGCAGGTC TTCCCGACGA TGACGCCGGT GAACTTCCCG | 1860 |
| CCGCCGTTGT TGTTTTGGAG CACGGAAAGA CGATGACGGA AAAAGAGATC GTGGATTACG | 1920 |
| TCGCCAGTCA AGTAACAACC GCGAAAAAGT TGCGCGGAGG AGTTGTGTTT GTGGACGAAG | 1980 |
| TACCGAAAGG TCTTACCGGA AAACTCGACG CAAGAAAAAT CAGAGAGATC CTCATAAAGG | 2040 |
| CCAAGAAGGG CGGAAAGTCC AAATTGTAAA ATGTAACTGT ATTCAGCGAT GACGAAATTC | 2100 |
| TTAGCTATTG TAATACTGCG ATGAGTGGCA GGGCGGGGCG TAATTTTTTT AAGGCAGTTA | 2160 |
| TTGGTGCCCT TAAACGCCTG GTGCTACGCC TGAATAAGTG ATAATAAGCG GATGAATGGC | 2220 |
| AGAAATTCGC CGGATCTTTG TGAAGGAACC TTACTTCTGT GGTGTGACAT AATTGGACAA | 2280 |
| ACTACCTACA GAGATTTAAA GCTCTAAGGT AAATATAAAA TTTTTAAGTG TATAATGTGT | 2340 |
| TAAACTACTG ATTCTAATTG TTTGTGTATT TTAGATTCCA ACCTATGGAA CTGATGAATG | 2400 |
| GGAGCAGTGG TGGAATGCCT TTAATGAGGA AAACCTGTTT TGCTCAGAAG AAATGCCATC | 2460 |
| TAGTGATGAT GAGGCTACTG CTGACTCTCA ACATTCTACT CCTCCAAAAA AGAAGAGAAA | 2520 |
| GGTAGAAGAC CCCAAGGACT TTCCTTCAGA ATTGCTAAGT TTTTTGAGTC ATGCTGTGTT | 2580 |
| TAGTAATAGA ACTCTTGCTT GCTTTGCTAT TTACACCACA AAGGAAAAAG CTGCACTGCT | 2640 |
| ATACAAGAAA ATTATGGAAA AATATTCTGT AACCTTTATA AGTAGGCATA ACAGTTATAA | 2700 |
| TCATAACATA CTGTTTTTTC TTACTCCACA CAGGCATAGA GTGTCTGCTA TTAATAACTA | 2760 |
| TGCTCAAAAA TTGTGTACCT TTAGCTTTTT AATTTGTAAA GGGGTTAATA AGGAATATTT | 2820 |
| GATGTATAGT GCCTTGACTA GAGATCATAA TCAGCCATAC CACATTTGTA GAGGTTTTAC | 2880 |
| TTGCTTTAAA AAACCTCCCA CACCTCCCCC TGAACCTGAA ACATAAAATG AATGCAATTG | 2940 |
| TTGTTGTTAA CTTGTTTATT GCAGCTTATA ATGGTTACAA ATAAAGCAAT AGCATCACAA | 3000 |
| ATTTCACAAA TAAAGCATTT TTTTCACTGC ATTCTAGTTG TGGTTTGTCC AAACTCATCA | 3060 |
| ATGTATCTTA TCATGTCTGG ATCCGTCGAC CGATGCCCTT GAGAGCCTTC AACCCAGTCA | 3120 |

```
GCTCCTTCCG GTGGGCGCGG GGCATGACTA TCGTCGCCGC ACTTATGACT GTCTTCTTTA    3180

TCATGCAACT CGTAGGACAG GTGCCGGCAG CGCTCTTCCG CTTCCTCGCT CACTGACTCG    3240

CTGCGCTCGG TCGTTCGGCT GCGGCGAGCG GTATCAGCTC ACTCAAAGGC GGTAATACGG    3300

TTATCCACAG AATCAGGGGA TAACGCAGGA AAGAACATGT GAGCAAAAGG CCAGCAAAAG    3360

GCCAGGAACC GTAAAAAGGC CGCGTTGCTG GCGTTTTTCC ATAGGCTCCG CCCCCCTGAC    3420

GAGCATCACA AAAATCGACG CTCAAGTCAG AGGTGGCGAA ACCCGACAGG ACTATAAAGA    3480

TACCAGGCGT TTCCCCCTGG AAGCTCCCTC GTGCGCTCTC CTGTTCCGAC CCTGCCGCTT    3540

ACCGGATACC TGTCCGCCTT TCTCCCTTCG GGAAGCGTGG CGCTTTCTCA ATGCTCACGC    3600

TGTAGGTATC TCAGTTCGGT GTAGGTCGTT CGCTCCAAGC TGGGCTGTGT GCACGAACCC    3660

CCCGTTCAGC CCGACCGCTG CGCCTTATCC GGTAACTATC GTCTTGAGTC CAACCCGGTA    3720

AGACACGACT TATCGCCACT GGCAGCAGCC ACTGGTAACA GGATTAGCAG AGCGAGGTAT    3780

GTAGGCGGTG CTACAGAGTT CTTGAAGTGG TGGCCTAACT ACGGCTACAC TAGAAGGACA    3840

GTATTTGGTA TCTGCGCTCT GCTGAAGCCA GTTACCTTCG GAAAAAGAGT TGGTAGCTCT    3900

TGATCCGGCA AACAAACCAC CGCTGGTAGC GGTGGTTTTT TTGTTTGCAA GCAGCAGATT    3960

ACGCGCAGAA AAAAGGATC TCAAGAAGAT CCTTTGATCT TTTCTACGGG GTCTGACGCT    4020

CAGTGGAACG AAAACTCACG TTAAGGGATT TTGGTCATGA GATTATCAAA AAGGATCTTC    4080

ACCTAGATCC TTTTAAATTA AAAATGAAGT TTTAAATCAA TCTAAAGTAT ATATGAGTAA    4140

ACTTGGTCTG ACAGTTACCA ATGCTTAATC AGTGAGGCAC CTATCTCAGC GATCTGTCTA    4200

TTTCGTTCAT CCATAGTTGC CTGACTCCCC GTCGTGTAGA TAACTACGAT ACGGGAGGGC    4260

TTACCATCTG GCCCCAGTGC TGCAATGATA CCGCGAGACC CACGCTCACC GGCTCCAGAT    4320

TTATCAGCAA TAAACCAGCC AGCCGGAAGG GCCGAGCGCA GAAGTGGTCC TGCAACTTTA    4380

TCCGCCTCCA TCCAGTCTAT TAATTGTTGC CGGGAAGCTA GAGTAAGTAG TTCGCCAGTT    4440

AATAGTTTGC GCAACGTTGT TGCCATTGCT ACAGGCATCG TGGTGTCACG CTCGTCGTTT    4500

GGTATGGCTT CATTCAGCTC CGGTTCCCAA CGATCAAGGC GAGTTACATG ATCCCCCATG    4560

TTGTGCAAAA AAGCGGTTAG CTCCTTCGGT CCTCCGATCG TTGTCAGAAG TAAGTTGGCC    4620

GCAGTGTTAT CACTCATGGT TATGGCAGCA CTGCATAATT CTCTTACTGT CATGCCATCC    4680

GTAAGATGCT TTTCTGTGAC TGGTGAGTAC TCAACCAAGT CATTCTGAGA ATAGTGTATG    4740

CGGCGACCGA GTTGCTCTTG CCCGGCGTCA ATACGGGATA ATACCGCGCC ACATAGCAGA    4800

ACTTTAAAAG TGCTCATCAT TGGAAAACGT TCTTCGGGGC GAAAACTCTC AAGGATCTTA    4860

CCGCTGTTGA GATCCAGTTC GATGTAACCC ACTCGTGCAC CCAACTGATC TTCAGCATCT    4920

TTTACTTTCA CCAGCGTTTC TGGGTGAGCA AAAACAGGAA GGCAAAATGC CGCAAAAAAG    4980

GGAATAAGGG CGACACGGAA ATGTTGAATA CTCATACTCT TCCTTTTTCA ATATTATTGA    5040

AGCATTTATC AGGGTTATTG TCTCATGAGC GGATACATAT TTGAATGTAT TTAGAAAAAT    5100

AAACAAATAG GGGTTCCGCG CACATTTCCC CGAAAAGTGC CACCTGACGC GCCCTGTAGC    5160

GGCGCATTAA GCGCGGCGGG TGTGGTGGTT ACGCGCAGCG TGACCGCTAC ACTTGCCAGC    5220

GCCCTAGCGC CCGCTCCTTT CGCTTTCTTC CCTTCCTTTC TCGCCACGTT CGCCGGCTTT    5280

CCCCGTCAAG CTCTAAATCG GGGGCTCCCT TTAGGGTTCC GATTTAGTGC TTTACGGCAC    5340

CTCGACCCCA AAAAACTTGA TTAGGGTGAT GGTTCACGTA GTGGGCCATC GCCCTGATAG    5400

ACGGTTTTTC GCCCTTTGAC GTTGGAGTCC ACGTTCTTTA ATAGTGGACT CTTGTTCCAA    5460

ACTGGAACAA CACTCAACCC TATCTCGGTC TATTCTTTTG ATTTATAAGG GATTTTGCCG    5520
```

```
ATTTCGGCCT ATTGGTTAAA AAATGAGCTG ATTTAACAAA AATTTAACGC GAATTTTAAC        5580

AAAATATTAA CGTTTACAAT TTCCCATTCG CCATTCAGGC TGCGCAACTG TTGGGAAGGG        5640

CGATCGGTGC GGGCCTCTTC GCTATTACGC CAGCCCAAGC TACCATGATA AGTAAGTAAT       5700

ATTAAGGTAC GTGGAGGTTT TACTTGCTTT AAAAAACCTC CCACACCTCC CCCTGAACCT       5760

GAAACATAAA ATGAATGCAA TTGTTGTTGT TAACTTGTTT ATTGCAGCTT ATAATGGTTA       5820

CAAATAAAGC AATAGCATCA CAAATTTCAC AAATAAAGCA TTTTTTTCAC TGCATTCTAG       5880

TTGTGGTTTG TCCAAACTCA TCAATGTATC TTATGGTACT GTAACTGAGC TAACATAA        5938
```

(2) INFORMATION FOR SEQ ID NO: 5:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (xi) SEQUENCE DESCRIPTION: SEQ ID NO: 5:

```
SNKRGCTGGG                                                               10
```

(2) INFORMATION FOR SEQ ID NO: 6:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (xi) SEQUENCE DESCRIPTION: SEQ ID NO: 6:

```
CGGGGCTGGC                                                               10
```

(2) INFORMATION FOR SEQ ID NO: 7:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (xi) SEQUENCE DESCRIPTION: SEQ ID NO: 7:

```
CTGGGCTGGG                                                               10
```

(2) INFORMATION FOR SEQ ID NO: 8:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "oligomer: oligo-apoAI-DRE"

(xi) SEQUENCE DESCRIPTION: SEQ ID NO: 8:

```
GGCCGGGGCT GGCTTATCAG CCTCCCAGCC CAGACC                                  36
```

(2) INFORMATION FOR SEQ ID NO: 9:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: other nucleic acid (A) DESCRIPTION: /desc = "oligomer: P450(I)"

(xi) SEQUENCE DESCRIPTION: SEQ ID NO: 9:

CACAGGGGCT GGGGAG          16

(2) INFORMATION FOR SEQ ID NO: 10:

(i) SEQUENCE CHARACTERISTICS:
      (A) LENGTH: 16 base pairs
      (B) TYPE: nucleic acid
      (C) STRANDEDNESS: double
      (D) TOPOLOGY: linear (ii) MOLECULE TYPE: other nucleic acid
      (A) DESCRIPTION: /desc = "oligomer: P450(II)"

(xi) SEQUENCE DESCRIPTION: SEQ ID NO: 10:

GACCCCAGCC TTCACA          16

(2) INFORMATION FOR SEQ ID NO: 11:

(i) SEQUENCE CHARACTERISTICS:
      (A) LENGTH: 26 base pairs
      (B) TYPE: nucleic acid
      (C) STRANDEDNESS: double
      (D) TOPOLOGY: linear (ii) MOLECULE TYPE: other nucleic acid
      (A) DESCRIPTION: /desc = "oligomer: AP1"

(xi) SEQUENCE DESCRIPTION: SEQ ID NO: 11:

GCAGTCACAG TGACTCAGCA GAATCT          26

(2) INFORMATION FOR SEQ ID NO: 12:

(i) SEQUENCE CHARACTERISTICS:
      (A) LENGTH: 26 base pairs
      (B) TYPE: nucleic acid
      (C) STRANDEDNESS: double
      (D) TOPOLOGY: linear (ii) MOLECULE TYPE: other nucleic acid
      (A) DESCRIPTION: /desc = "oligomer: AP2"

(xi) SEQUENCE DESCRIPTION: SEQ ID NO: 12:

GATCGAACTG ACCGCCCGCG GCCCGT          26

(2) INFORMATION FOR SEQ ID NO: 13:

(i) SEQUENCE CHARACTERISTICS:
      (A) LENGTH: 17 base pairs
      (B) TYPE: nucleic acid
      (C) STRANDEDNESS: double
      (D) TOPOLOGY: linear (ii) MOLECULE TYPE: other nucleic acid
      (A) DESCRIPTION: /desc = "oligomer: SP1"

(xi) SEQUENCE DESCRIPTION: SEQ ID NO: 13:

CTGCGGGGCG GGGCAGA          17

(2) INFORMATION FOR SEQ ID NO: 14:

(i) SEQUENCE CHARACTERISTICS:
      (A) LENGTH: 15 base pairs
      (B) TYPE: nucleic acid
      (C) STRANDEDNESS: double
      (D) TOPOLOGY: linear (ii) MOLECULE TYPE: other nucleic acid -continued

```
        (A) DESCRIPTION:   /desc = "oligomer: oligo-AhR"

(xi) SEQUENCE DESCRIPTION: SEQ ID NO: 14:

AGTTGCGTGA GAAGA                                                    15

(2) INFORMATION FOR SEQ ID NO: 15:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: other nucleic acid
        (A) DESCRIPTION:   /desc = "oligomer: oligo-M1,
            mutated apoAI-DRE"

(xi) SEQUENCE DESCRIPTION: SEQ ID NO: 15:

TGGTGGCCGG GACTAGCTTA TGGT                                          24

(2) INFORMATION FOR SEQ ID NO: 16:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (xi) SEQUENCE DESCRIPTION: SEQ ID NO: 16:

CCCAGCCCAG                                                          10

(2) INFORMATION FOR SEQ ID NO: 17:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: other nucleic acid
        (A) DESCRIPTION:   /desc = "oligomer: mutated
            apoAI-DRE"

(xi) SEQUENCE DESCRIPTION: SEQ ID NO: 17:

GGCATTTTAC TTATTATCAG CCTAAACTAA ACTACC                              36
```